United States Patent
Bonutti et al.

(10) Patent No.: US 9,173,647 B2
(45) Date of Patent: Nov. 3, 2015

(54) TISSUE FIXATION SYSTEM

(75) Inventors: Peter M. Bonutti, Effingham, IL (US);
Glen A. Phillips, Effingham, IL (US);
Larry Crainich, Charlestown, NH (US)

(73) Assignee: P Tech, LLC, Effingham, IL (US)

( * ) Notice: Subject to any disclaimer, the term of this patent is extended or adjusted under 35 U.S.C. 154(b) by 196 days.

(21) Appl. No.: 11/358,311

(22) Filed: Feb. 21, 2006

(65) Prior Publication Data
US 2006/0229623 A1    Oct. 12, 2006

Related U.S. Application Data

(60) Provisional application No. 60/655,140, filed on Feb. 22, 2005.

(51) Int. Cl.
| A61B 17/56 | (2006.01) |
| A61B 17/02 | (2006.01) |
| A61B 17/04 | (2006.01) |
| A61B 17/68 | (2006.01) |

(Continued)

(52) U.S. Cl.
CPC ......... *A61B 17/0218* (2013.01); *A61B 17/0469* (2013.01); *A61B 17/683* (2013.01); *A61B 17/8869* (2013.01); *A61B 17/1615* (2013.01); *A61B 17/7053* (2013.01); *A61B 17/842* (2013.01); *A61B 2017/0409* (2013.01); *A61B 2017/2926* (2013.01); *A61F 2/08* (2013.01); *A61F 2/28* (2013.01); *A61F 2/442* (2013.01); *A61F 2002/2817* (2013.01); *A61F 2002/30062* (2013.01); *A61F 2002/30677* (2013.01); *A61F 2002/444* (2013.01); *A61F 2002/4435* (2013.01); *A61F 2210/0004* (2013.01); *A61F 2310/00293* (2013.01)

(58) Field of Classification Search
USPC ......... 606/72, 69, 74, 916, 103, 60, 86 R, 99, 606/232
See application file for complete search history.

(56) References Cited

U.S. PATENT DOCUMENTS

| 319,296 A | 6/1885 | Molesworth |
| 668,878 A | 2/1901 | Jensen |

(Continued)

FOREIGN PATENT DOCUMENTS

| CA | 2641580 | 8/2007 |
| CA | 2680827 | 9/2008 |

(Continued)

OTHER PUBLICATIONS

Petition for Inter Partes Review of U.S. Pat. No. 5,980,559, IPR 2013-00603, Filing Date Sep. 24, 2013.

(Continued)

*Primary Examiner* — Sameh Boles

(57) ABSTRACT

A tissue fixation system is provided for dynamic and rigid fixation of tissue. A fastener connected with an elongate fastening member, such as a cable, wire, suture, rod, or tube, is moved through a passage between opposite sides of tissue. The fastener is provided with a groove that accommodates at least a portion of the fastening member to reduce the profile during the movement through the passage. The fastener is then pivoted to change its orientation. A second fastener can then be connected with the fastening member. While tension is maintained in the fastening member, the fasteners are secured against relative movement. This may be done by deforming the fastening member, either the first or second fasteners, or a bushing placed against the second fastener.

48 Claims, 41 Drawing Sheets

(51) Int. Cl.
*A61B 17/88* (2006.01)
*A61B 17/16* (2006.01)
*A61B 17/70* (2006.01)
*A61B 17/84* (2006.01)
*A61B 17/29* (2006.01)
*A61F 2/08* (2006.01)
*A61F 2/28* (2006.01)
*A61F 2/44* (2006.01)
*A61F 2/30* (2006.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1939 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A * | 8/1950 | Brawand .................... 24/129 R |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss et al. |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston et al. |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kalnberz et al. |
| 4,156,574 A | 5/1979 | Boden |
| 4,164,794 A | 8/1979 | Spector et al. |
| 4,171,544 A | 10/1979 | Hench et al. |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. et al. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | Van der Zat et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,493,317 A | 1/1985 | Klaue |
| 4,495,664 A | 1/1985 | Bianquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,100 A | 12/1986 | Somers |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,691,741 A | 9/1987 | Affa et al. |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,257 A | 5/1988 | Tormala |
| 4,749,585 A | 6/1988 | Greco et al. |
| 4,750,492 A | 6/1988 | Jacobs |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |
| 4,792,336 A | 12/1988 | Hlavacek et al. |
| 4,817,591 A | 4/1989 | Klaue |
| 4,822,224 A | 4/1989 | Carl et al. |
| 4,823,794 A | 4/1989 | Pierce |
| 4,832,025 A | 5/1989 | Coates |

(56) References Cited

U.S. PATENT DOCUMENTS

| | | |
|---|---|---|
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A | 5/1990 | Sapega et al. |
| 4,924,866 A | 5/1990 | Yoon |
| 4,932,960 A | 6/1990 | Green et al. |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,950,285 A | 8/1990 | Wilk |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurst |
| 4,963,151 A | 10/1990 | Ducheyne et al. |
| 4,966,583 A | 10/1990 | Debbas |
| 4,968,315 A | 11/1990 | Gatturna |
| 4,968,317 A | 11/1990 | Tormala |
| 4,969,888 A | 11/1990 | Scholten et al. |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A | 5/1991 | Goble et al. |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold et al. |
| 5,037,422 A | 8/1991 | Hayhurst et al. |
| 5,041,093 A | 8/1991 | Chu |
| 5,041,114 A | 8/1991 | Chapman et al. |
| 5,041,129 A | 8/1991 | Hayhurst et al. |
| 5,046,513 A | 9/1991 | Gattuma et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid et al. |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,141,520 A | 8/1992 | Goble et al. |
| 5,147,362 A | 9/1992 | Goble |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,385 A | 1/1993 | Sontag |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |
| 5,197,971 A | 3/1993 | Bonutti |
| 5,203,784 A | 4/1993 | Ross et al. |
| 5,203,787 A | 4/1993 | Noblitt et al. |
| 5,208,950 A | 5/1993 | Merritt |
| 5,209,776 A | 5/1993 | Bass et al. |
| 5,217,493 A | 6/1993 | Raad et al. |
| 5,219,359 A | 6/1993 | McQuilkin et al. |
| 5,226,899 A | 7/1993 | Lee et al. |
| 5,234,006 A | 8/1993 | Eaton et al. |
| 5,234,425 A | 8/1993 | Fogarty et al. |
| 5,234,443 A | 8/1993 | Phan |
| 5,236,438 A | 8/1993 | Wilk |
| 5,236,445 A | 8/1993 | Hayhurst |
| 5,242,902 A | 9/1993 | Murphy et al. |
| 5,254,113 A | 10/1993 | Wilk |
| 5,258,007 A | 11/1993 | Spetzler et al. |
| 5,258,015 A | 11/1993 | Li et al. |
| 5,258,016 A | 11/1993 | DiPoto et al. |
| 5,261,886 A | 11/1993 | Chesterfield |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,281,235 A | 1/1994 | Haber et al. |
| 5,282,832 A | 2/1994 | Toso et al. |
| 5,290,281 A | 3/1994 | Tschakaloff |
| 5,304,119 A | 4/1994 | Balaban et al. |
| 5,306,280 A | 4/1994 | Bregen et al. |
| 5,306,301 A | 4/1994 | Graf et al. |
| 5,315,741 A | 5/1994 | Dubberke |
| 5,318,588 A | 6/1994 | Horzewski et al. |
| 5,320,611 A | 6/1994 | Bonutti et al. |
| 5,324,308 A | 6/1994 | Pierce |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,336,231 A | 8/1994 | Adair |
| 5,336,240 A | 8/1994 | Metzler et al. |
| 5,339,799 A | 8/1994 | Kami et al. |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,366,480 A | 11/1994 | Corriveau et al. |
| 5,370,646 A | 12/1994 | Reese et al. |
| 5,370,660 A | 12/1994 | Weinstein et al. |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry et al. |
| 5,383,883 A | 1/1995 | Wilk et al. |

(56) References Cited

U.S. PATENT DOCUMENTS

| | | |
|---|---|---|
| 5,383,905 A | 1/1995 | Golds et al. |
| 5,391,173 A | 2/1995 | Wilk |
| 5,395,308 A | 3/1995 | Fox et al. |
| 5,397,311 A | 3/1995 | Walker et al. |
| 5,400,805 A | 3/1995 | Warren |
| 5,403,312 A | 4/1995 | Yates et al. |
| 5,403,348 A | 4/1995 | Bonutti |
| 5,405,359 A * | 4/1995 | Pierce ............ 606/232 |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker et al. |
| 5,423,796 A | 6/1995 | Shikhman et al. |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr et al. |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez et al. |
| 5,456,722 A | 10/1995 | McLeod et al. |
| 5,458,653 A | 10/1995 | Davidson |
| 5,462,561 A | 10/1995 | Voda |
| 5,464,424 A | 11/1995 | O'Donnell, Jr. |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,318 A | 3/1996 | Howland |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,578,046 A | 11/1996 | Liu |
| 5,580,344 A | 12/1996 | Hasson |
| 5,584,835 A | 12/1996 | Greenfield |
| 5,584,839 A | 12/1996 | Gieringer |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,321 A * | 7/1997 | McDevitt ............ 606/232 |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |

(56) References Cited

U.S. PATENT DOCUMENTS

| | | |
|---|---|---|
| 5,800,537 A | 9/1998 | Bell |
| 5,807,403 A | 9/1998 | Beyar et al. |
| 5,810,849 A | 9/1998 | Kontos Slavros |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakural et al. |
| 5,839,899 A | 11/1998 | Robinson |
| 5,843,084 A | 12/1998 | Hart |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige et al. |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A | 8/1999 | Fong |
| 5,941,900 A | 8/1999 | Bonutti |
| 5,941,901 A | 8/1999 | Egan |
| 5,944,750 A | 8/1999 | Tanner |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto et al. |
| 5,961,499 A | 10/1999 | Bonutti |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,068,648 A | 5/2000 | Cole |
| 6,077,277 A | 6/2000 | Mollenauer et al. |
| 6,077,292 A | 6/2000 | Bonutti |
| 6,080,161 A | 6/2000 | Eaves, III et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,299 B1 | 1/2001 | Bonutti |
| 6,171,307 B1 | 1/2001 | Orlich |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green |
| 6,200,322 B1 | 3/2001 | Branch et al. |
| 6,217,591 B1 | 4/2001 | Egan et al. |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,238,395 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti et al. |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti |
| 6,371,957 B1 | 4/2002 | Amrein et al. |
| 6,409,742 B1 | 6/2002 | Fulton, III |
| 6,409,743 B1 | 6/2002 | Fenton, Jr. |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |

(56) References Cited

U.S. PATENT DOCUMENTS

| | | | |
|---|---|---|---|
| 6,461,360 B1 | 10/2002 | Adam |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel et al. |
| 6,527,774 B2 | 3/2003 | Lieberman |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,551,343 B1 | 4/2003 | Tormala |
| 6,554,852 B1 | 4/2003 | Oberlander |
| 6,557,426 B2 | 5/2003 | Reinemann et al. |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,592,609 B1 | 7/2003 | Bonutti |
| 6,594,517 B1 | 7/2003 | Nevo |
| 6,602,293 B1 | 8/2003 | Biermann |
| 6,605,090 B1 | 8/2003 | Trieu |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 * | 11/2003 | Fallin et al. ............ 606/232 |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,830,589 B2 | 12/2004 | Erickson |
| 6,860,885 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,128,763 B1 | 10/2006 | Blatt |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 * | 5/2007 | Reese ................ 606/232 |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,326,200 B2 | 2/2008 | Trieu |
| 7,329,263 B2 | 2/2008 | Bonutti |
| 7,335,205 B2 | 2/2008 | Aeshcliamann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Raterman |
| 7,597,705 B2 | 10/2009 | Forsberg |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,771,314 B2 | 7/2014 | Crombie |
| 8,845,699 B2 | 9/2014 | Bonutti |
| 2001/0002440 A1 | 5/2001 | Bonutti |
| 2001/0008971 A1 | 7/2001 | Schwartz |
| 2001/0009250 A1 | 7/2001 | Herman et al. |
| 2001/0041916 A1 | 11/2001 | Bonutti |
| 2001/0056287 A1 | 12/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029067 A1 | 3/2002 | Bonutti |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0058966 A1 | 5/2002 | Tormala |
| 2002/0062153 A1 | 5/2002 | Paul et al. |
| 2002/0087189 A1 | 7/2002 | Bonutti |
| 2002/0103495 A1 | 8/2002 | Cole |
| 2002/0120269 A1 | 8/2002 | Lange |
| 2002/0123750 A1 | 9/2002 | Eisermann et al. |
| 2002/0161439 A1 | 10/2002 | Strobel |
| 2002/0183762 A1 | 12/2002 | Anderson et al. |
| 2002/0188301 A1 | 12/2002 | Dallara et al. |
| 2003/0039196 A1 | 2/2003 | Nakamura et al. |
| 2003/0040758 A1 | 2/2003 | Wang et al. |
| 2003/0065361 A1 * | 4/2003 | Dreyfuss .............. 606/232 |
| 2003/0083667 A1 | 5/2003 | Ralph |
| 2003/0097148 A1 | 5/2003 | Valimaa |
| 2003/0105474 A1 | 6/2003 | Bonutti |
| 2003/0118518 A1 | 6/2003 | Hahn et al. |
| 2003/0125749 A1 | 7/2003 | Yuan |
| 2003/0158555 A1 | 8/2003 | Sanders |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195514 A1 | 10/2003 | Trieu |
| 2003/0195530 A1 | 10/2003 | Thill |
| 2003/0195565 A1 | 10/2003 | Bonutti |
| 2003/0204204 A1 | 10/2003 | Bonutti |

(56) References Cited

U.S. PATENT DOCUMENTS

| | | |
|---|---|---|
| 2003/0208203 A1 | 11/2003 | Lim |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0024459 A1 | 2/2004 | Ferree |
| 2004/0030341 A1 | 2/2004 | Aeschlimann et al. |
| 2004/0034357 A1 | 2/2004 | Beane et al. |
| 2004/0039392 A1 | 2/2004 | Trieu |
| 2004/0049207 A1 | 3/2004 | Goldfarb |
| 2004/0097939 A1 | 5/2004 | Bonutti |
| 2004/0098050 A1 | 5/2004 | Foerster et al. |
| 2004/0102788 A1 | 5/2004 | Huebner |
| 2004/0116963 A1 | 6/2004 | Lattouf |
| 2004/0138703 A1 | 7/2004 | Alleyne |
| 2004/0138705 A1 | 7/2004 | Heino |
| 2004/0143334 A1 | 7/2004 | Ferree |
| 2004/0167548 A1 | 8/2004 | Bonutti |
| 2004/0172063 A1 | 9/2004 | Li |
| 2004/0186471 A1 | 9/2004 | Trieu |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2005/0033362 A1 | 2/2005 | Grafton |
| 2005/0033366 A1* | 2/2005 | Cole et al. ............... 606/232 |
| 2005/0038514 A1 | 2/2005 | Helm et al. |
| 2005/0043733 A1 | 2/2005 | Eisermann |
| 2005/0043796 A1 | 2/2005 | Grant et al. |
| 2005/0065409 A1* | 3/2005 | de la Torre et al. ........... 600/204 |
| 2005/0070765 A1 | 3/2005 | Abdelgany |
| 2005/0071012 A1 | 3/2005 | Serhan et al. |
| 2005/0075644 A1 | 4/2005 | DiPoto |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0125072 A1 | 6/2005 | Kolb |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0234460 A1 | 10/2005 | Miller |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0256582 A1 | 11/2005 | Ferree |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2005/0283246 A1 | 12/2005 | Cauthen |
| 2006/0009846 A1 | 1/2006 | Trieu |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti |
| 2006/0189982 A1 | 8/2006 | Lange |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235413 A1 | 10/2006 | Denham |
| 2006/0235470 A1 | 10/2006 | Bonutti |
| 2006/0241695 A1 | 10/2006 | Bonutti |
| 2006/0264953 A1 | 11/2006 | Falahee |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0118129 A1 | 5/2007 | Fraser et al. |
| 2007/0198555 A1 | 8/2007 | Friedman et al. |
| 2007/0233092 A1 | 10/2007 | Falahee |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0097448 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 93/23094 | 11/1993 |
| WO | WO9408642 | 4/1994 |
| WO | 95/16398 | 6/1995 |
| WO | WO 95/31941 | 11/1995 |
| WO | WO9614802 | 5/1996 |
| WO | WO9712779 | 4/1997 |
| WO | 97/49347 | 12/1997 |
| WO | WO 97/49347 | 12/1997 |
| WO | WO9811838 | 3/1998 |
| WO | WO9826720 | 6/1998 |
| WO | WO02053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |

(56) References Cited

FOREIGN PATENT DOCUMENTS

| WO | 2009124215 | 10/2009 |
|---|---|---|
| WO | WO2010099222 | 2/2010 |

OTHER PUBLICATIONS

Declaration of David Kaplan, PH.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for USP 8,147,514, from IPR 2013-00632, dated Sep. 23, 2013 (exhibit 1009).
Declaration of Steve Jordan for USP 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for USP 5921986, from IPR 2013-00632, dated Sep. 24, 2013 (exhibit 1010).
Declaration of Steve Jordan for USP 5921986, from IPR 2013-00633, dated Sep. 24, 2013 (exhibit 1007).
Declaration of Dr. Steve E. Jordan for USP 8,147,514, from IPR 2013-00631, dated Sep. 23, 2013.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, published Aug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64 Feb. 1998.
Packer et al, Repair of Acute Scapho-Lunate Dissociation Facilitated by the "TAG" Suture Anchor, Journal of Hand Surgery (British and European Volume, 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb.), 1998: pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb.), 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.

(56) References Cited

OTHER PUBLICATIONS

Fellinger, et al, Radial avulsion of the triangular fibrocartilage complex in acute wrist trauma: a new technique for arthroscopic repair, Jun. 1997, Arthroscopy vol. 13 No. 3 p. 370-4.

Hecker et al, Pull-out strength of suture anchors for rotator cuff and Bankart lesion repairs, Nov.-Dec. 1997, The American Journal of Sports Medicine, vol. 21 No. 6 p. 874-9.

Hernigou et al, Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.

Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.

Mosca et al, Calcaneal Lengthening for Valgus Deformity of the Hindfoot: Results in Children Who Had Severe, Symptomatic Flatfoot and Skewfoot, J Bone Joint Surg., 1195—p. 499-512.

Murphycet al, Radial Opening Wedge Osteotomy in Madelung's Deformity, J. Hand Surg, vol. 21 A No. 6 Nov. 1996, p. 1035-44.

Biomet, Stanmore Modular Hip, J. Bone Joint Surg., vol. 76-B : No. Two, Mar. 1994.

Intl Prelim Rep on Patentability and Written Opinion for PCT/US10/25263 dated Aug. 30, 2011.

European Search Report dated Sep. 10, 2012 for EP08732724.3 (046).

010-3 Copending U.S. Appl. No. 11/932,907—RCE Response Sep. 15, 2011.

027 Copending U.S. Appl. No. 11/258,795 Non-Final Office Action mailed Apr. 26, 2011.

046 Copending U.S. Appl. No. 11/689,670, RCE Response Sep. 19, 2011.

003-1 Copending U.S. Appl. No. 10/614,352, Final Office Action Jul. 12, 2010.

007-2 Copending U.S. Appl. No. 11/932,602 Final Response to Office Action Jun. 10, 2011.

039 Copending U.S. Appl. No. 11/671,556 Response filed Aug. 23, 2010.

Co-pending U.S. Appl. No. 11/438,537, Supplemental Final Rejection mailed Sep. 25, 2009.

IPR—International Publication WO/2008/116203, published Sep. 22, 2009 for PCT/US08/57948.

ISR—International Search Report WO/2008/116203, published Dec. 24, 2008 for PCT/US08/57948.

IPER—Internation Preliminary Report on Patentability, WO/2008/116203, published Sep. 22, 2009 for PCT/US08/57948.

Written Opinion WO/2008/116203 dated Oct. 23, 2008 for PCT/US08/57948.

IPR—International Publication WO2009/029908, published May 3, 2009 for PCT/US08/74941.

ISR—International Search Report, WO2009/029908, published May 3, 2009 for PCT/US08/74941.

IPER—Internation Preliminary Report on Patentability, WO2009/029908, published Mar. 2, 2010 for PCT/US08/74941.

Written Opinion WO2009/029908 dated Feb. 28, 2010 for PCT/US08/74941.

International Search Report PCT/US2010/025263 completed Apr. 13, 2010.

Written Opinion for PCT/US2010/025263 completed Apr. 13, 2010.

\* cited by examiner

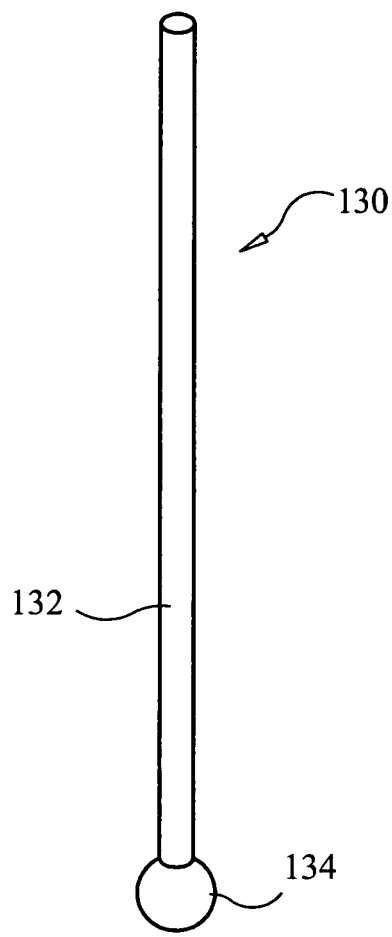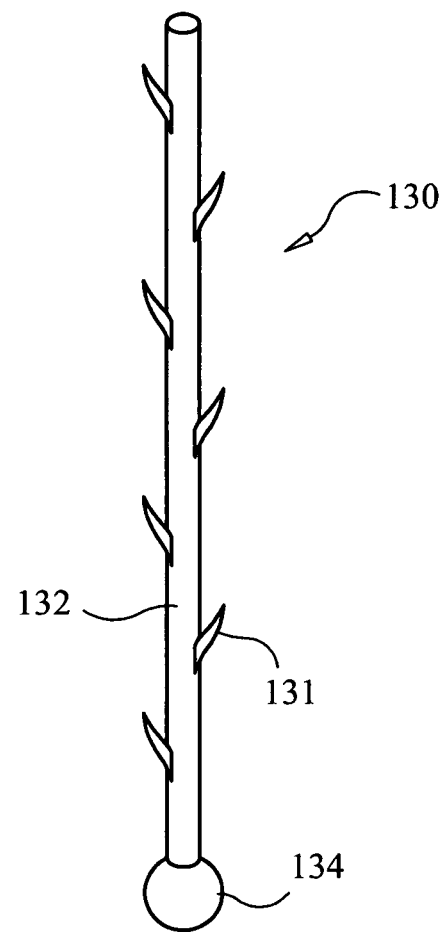
FIG. 9A    FIG. 9B
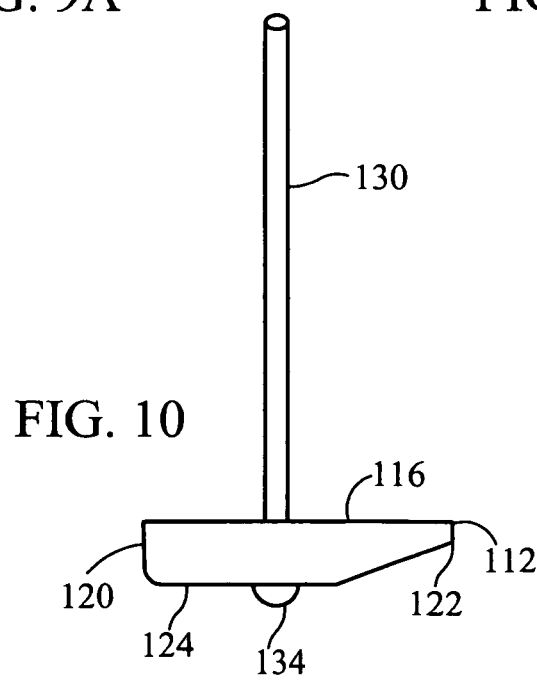
FIG. 10

TISSUE FIXATION SYSTEM

CROSS-REFERENCE TO RELATED APPLICATION

This Application claims the benefit of U.S. Provisional Patent Application No. 60/655,140, filed Feb. 22, 2005, entitled TISSUE FIXATION SYSTEM AND METHOD, the content of which is incorporated by reference in its entirety.

FIELD OF THE INVENTION

The invention relates to a system and method for fixation and stabilization of tissue. In particular, the invention relates to minimally invasive bone fracture fixation and stabilization.

BACKGROUND OF THE INVENTION

It is well-known in the medical arts that applying pressure to tissue helps during the healing process. Incised or torn soft tissue, for example, may be approximated with bandages, sutures, or staples. Proper and more rapid healing of broken or fractured bones likewise may be facilitated by applying constant pressure to the bone. For instance, physicians may insert pins, screws, or bolts in the area of the fracture in order to apply pressure to the fracture.

However, inserting screws through or around fractures can be complex and time-consuming. For example, the process of inserting a screw typically involves multiple steps conducted from multiple incisions or openings that provide access to the treated bone or tissue, including the steps of drilling holes, measuring the relevant distances to determine the appropriate screw selection, tapping the hole to establish threads, and screwing the screw into the hole.

In addition to the length and complexity of the process, bone screws also may lose their grip and strip out of the bone. In addition, currently available lag screws also typically provide only one side of cortex fixation and are generally not suited for percutaneous surgery. Moreover, when placing the screws in the bone, the physician may not accurately set the screw into the distal hole or may miss the distal hole completely, thereby resulting in the screw stripping the threads or breaking the bone.

Many devices and instruments have been disclosed to fasten soft and hard tissue for enhanced healing or tissue reconstruction. Examples of such devices include bone plates, bone wraps, external bone supports, and the like.

For example, U.S. Pat. No. 5,921,986, the contents of which are incorporated herein by reference, discloses a bone suture and associated methods for implantation and fracture fixation. The '986 Patent describes fasteners and anchors used in conjunction with an elongate fixation element, such as a suture. In some cases, it may be advantageous to use more rigid fixation elements.

Accordingly, a need exists for a tissue fixation instrument which can provide flexible or rigid fixation of tissue while accessing the tissue from a small skin portal.

SUMMARY OF THE INVENTION

The present invention relates to a tissue fixation system. The system comprises an elongate fastening member and a fastener moveable with respect to the elongate fastening member from a first orientation to a second orientation, the fastener having a body with a tissue contacting surface that includes a groove configured and dimensioned to receive a portion of the elongate member in the first orientation. The system can also include a second fastener or other means for maintaining tension in the elongate fastening member.

A biasing means can be provided to maintain the fastener in the first orientation. The biasing means can be an adhesive between the groove and the portion of the elongate fastening member received in the groove. The biasing means could also be a frangible connection between the groove and the portion of the elongate fastening member received in the groove.

The fastener body can have a free surface opposite the tissue contacting surface, with the free surface including a channel configured and dimensioned to receive a portion of the elongate member in the first orientation. The fastener body can also include a through bore extending from the tissue contacting surface through the free surface.

In one embodiment, the fastener body includes leading and trailing ends. The leading end can be tapered or otherwise shaped to facilitate insertion. The groove terminates at the through bore and extends toward one of the leading and trailing ends and the channel terminates at the through bore and extends toward the other of the leading and trailing ends. In an exemplary embodiment, the groove extends toward the leading end and the channel extends toward the trailing end.

The free surface of the fastener body can be provided with a well surrounding the through bore. The well can be configured and dimensioned to receive at least a portion of the stop. A distal end of the elongate fastening member can include a stop larger than the through bore.

The present invention also relates to a medical instrument or device for securing the fastener with respect to the elongate fastening member. The medical device tensions the elongate fastening member and crimps either the fastener or a bushing. Another aspect of the invention relates to methods of tissue fixation using the disclosed tissue fixation systems.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 9A shows an elongate fastening member according to the present invention;

FIG. 9B shows an elongate fastening member including expandable members;

FIG. 10 shows a fastener in a second orientation with respect to an elongate fastening member;

DETAILED DESCRIPTION OF THE INVENTION

The present invention provides a tissue fixation system for dynamic and rigid fixation of tissue. The system can be utilized for the fixation and stabilization of body tissue, including soft tissue to soft tissue, soft tissue to bone, and bone to bone. The surgical system can additionally be used to affix implants and grafts to body tissue. The system can access and treat fractured, incised or torn tissue, or the like, from one access area (i.e., from only one opening to the tissue to be fastened) instead of requiring two or more openings. That is, the system is a linear fixation system that can be used with a single, small incision or portal in the skin or other soft tissue to gain access to the fractured bone. The fixation system may be an all-in-one system, packaged as a system kit, for creating a passage in tissue, positioning fasteners, and tensioning an elongate fastening member, like a suture, thread, cable, wire, rod, or pin. The individual components of the system can either be reusable or single use components.

Figure 1:
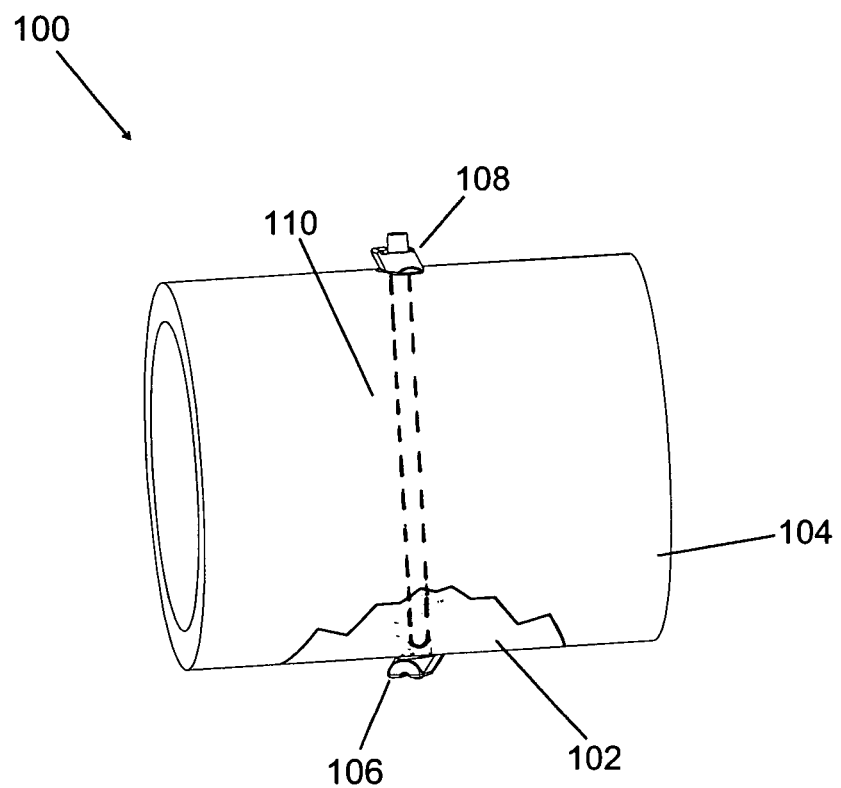
FIG. 1 shows a schematic illustration of a tissue fixation system according to the present invention utilized for fracture fixation.
Figure 2:
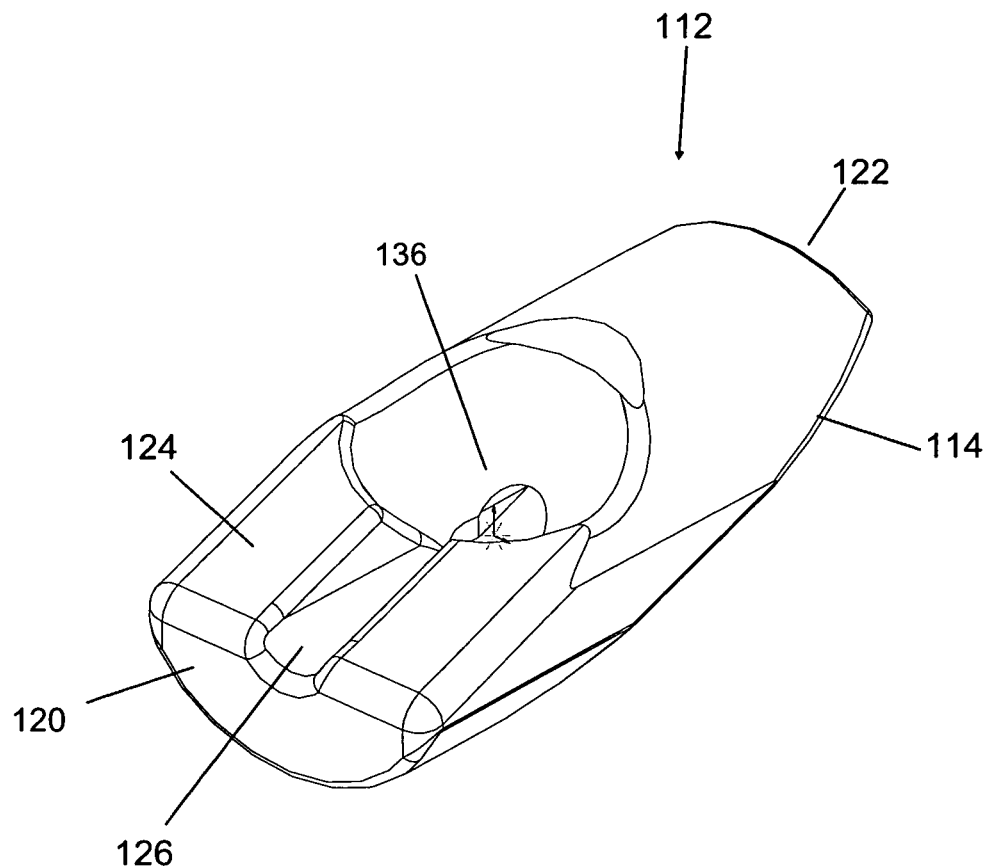
FIG. 2 shows a perspective view of a fastener according to the present invention.
Figure 3:
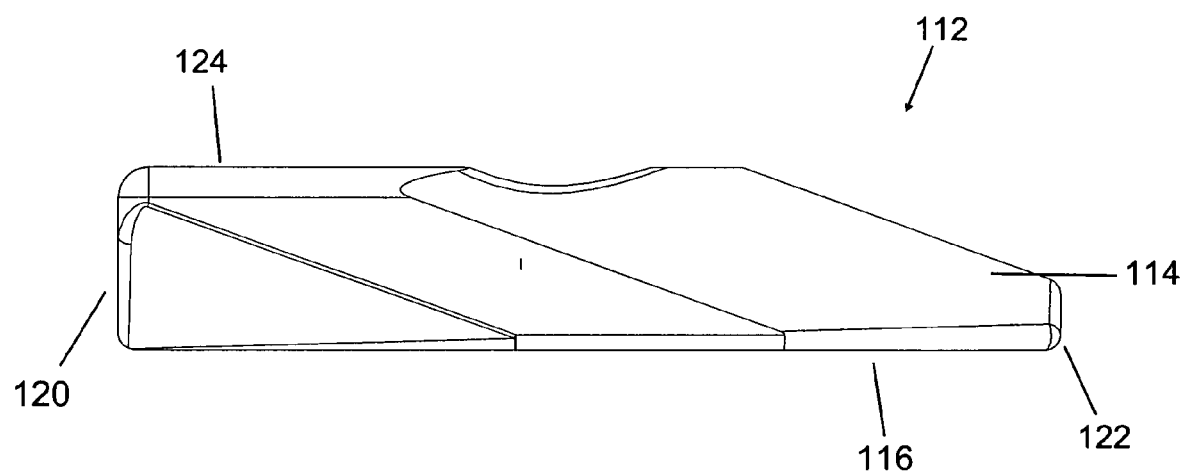
FIG. 3 shows a side view of the fastener of FIG. 2.
Figure 4:
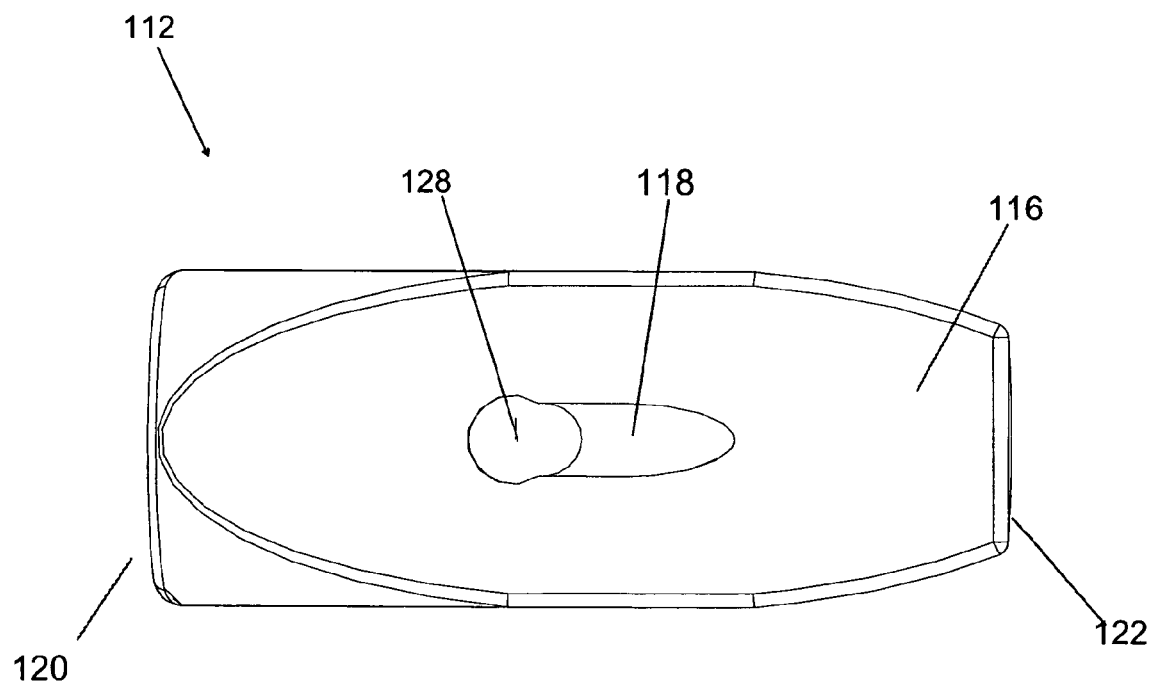
FIG. 4 shows a bottom view of the fastener of FIG. 2.

Referring now to the drawing figures in which like reference designators refer to like elements, FIG. 1 shows an exemplary embodiment of a tissue fixation system 100 according to the present invention. A fractured portion 102 of a bone 104 is approximated by system 100. Use of system 100 is not limited to any particular type of fracture. Furthermore, use of system 100 is not limited to fracture fixation. In other words, system 100 can be utilized for other tissue fixation applications (such as soft tissue) or similar clinical indications. Examples of such tissue includes, are not limited to, muscle, cartilage, ligament, tendon, skin, etc. Also, the tissue may be stomach tissue, and the system may be used during bariatric surgery, like stomach stapling. Additionally, the system 100 can be used for the fixation of implants to tissue.

In this regard, the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

Although the invention is described primarily on a macroscopic level, it is also envisioned that the present invention can be used for microscopic applications. For example, in the repair of nerve tissue, individual cells or fibers may need to be repaired. Similarly, muscle repair may require tightening of individual muscle fibers.

System 100 includes a distal fastener 106 contacting fracture portion 102, a proximal fastener 108 contacting bone 104, and an elongate fastening member 110 extending through the fracture and coupling distal and proximal fasteners 106, 108. Tension is maintained in elongate fastening member 110 to press fasteners 106, 108 against opposite sides of bone 104 with a desired force. This force presses fracture portion 102 against bone 104 firmly together to promote healing of the fracture. If desired, buttons or other force distributing members could be provided between fasteners 106, 108 and the bone. Although FIG. 1 shows distal and proximal fasteners 106, 108 as having the same construction, they could have differing construction. However, for convenience and practical purposes, it may be beneficial if distal and proximal fasteners 106 and 108 have substantially the same construction.

Figure 5:
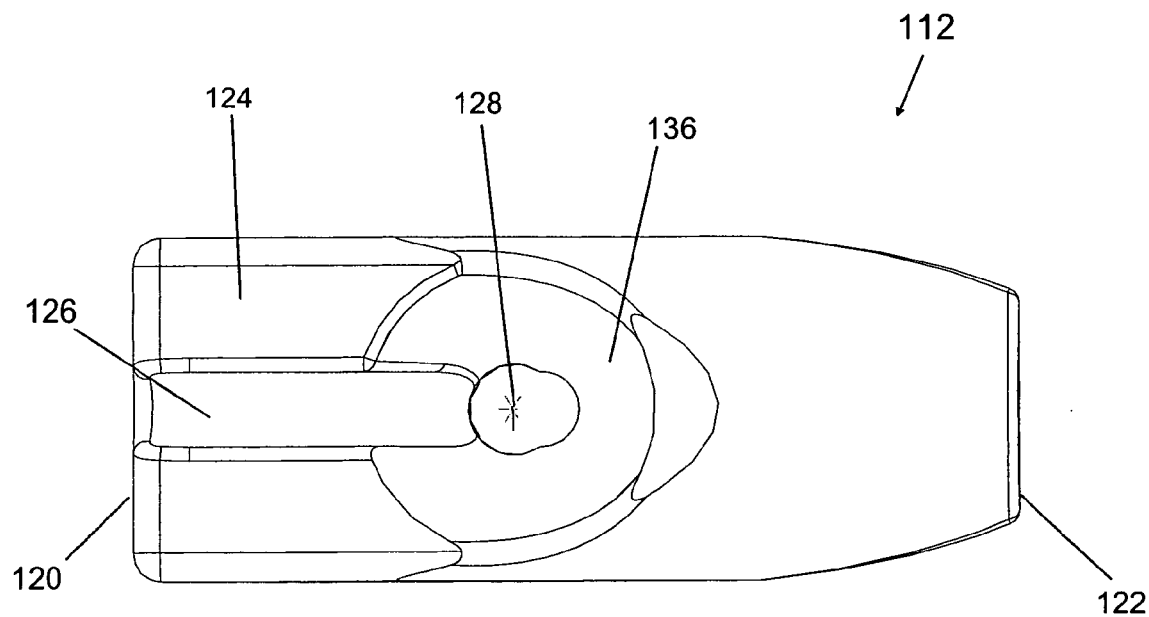
FIG. 5 shows a top view of the fastener of FIG. 2.
Figure 6:
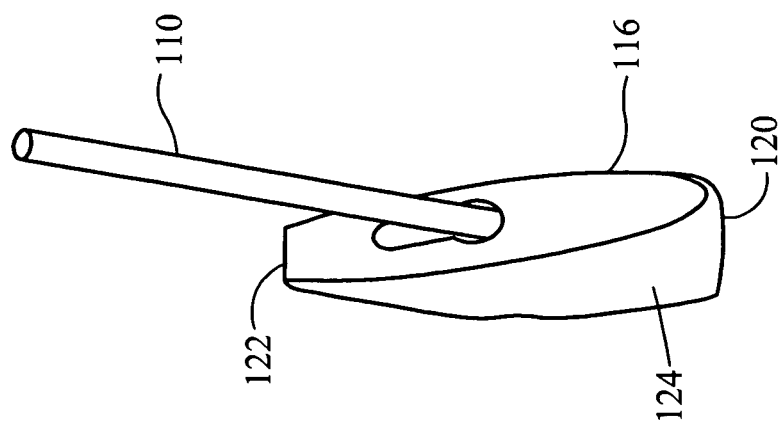
FIG. 6 shows a fastener and elongate fastening member with the fastener in a first orientation with respect to the elongate fastening member.

FIGS. 2-5 show an exemplary embodiment of a fastener 112 that can be used as part of system 100, i.e. as either or both of distal and proximal fasteners 106, 108. Fastener 112 has a body 114 that is configured and dimensioned to facilitate implantation through minimally invasive procedures, e.g. through a cannula or sleeve. In particular, body 114 includes a tissue contacting surface 116 that is provided with groove 118 that receives a portion of elongate fastening member 110 when fastener 112 is in a first orientation with respect to elongate fastening member 110. This is seen in FIG. 6. The accommodation of elongate fastening member 110 within groove 118 helps to minimize the profile of the assembly of fastener 112 and elongate fastening member 110. The reduced profile can be more readily passed through a cannula or sleeve. If desired, an adhesive can be provided within groove 118 to bias fastener 112 in the first orientation. Alternatively, a frangible connection can be provided between groove 118 and the portion of elongate fastening member 110. This frangible connection keeps fastener 112 in the first orientation with respect to elongate fastening member 110 until it is broken.

Figure 8:
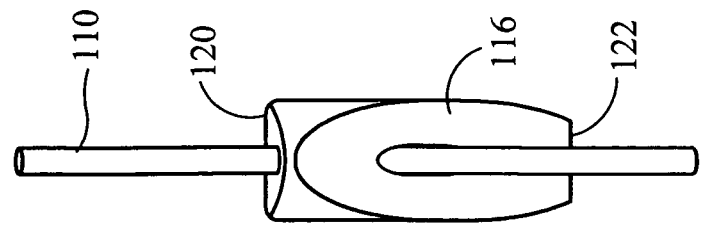
FIG. 8 shows a back view of the fastener and elongate fastening member of FIG. 7.
Figure 7:
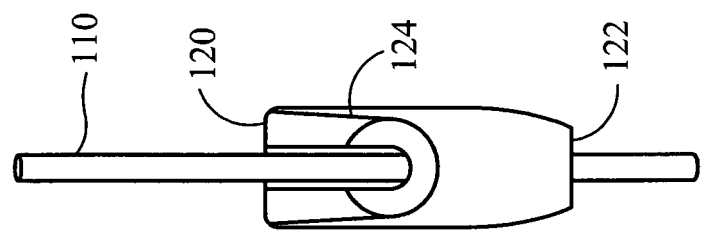
FIG. 7 shows a front view of a fastener in the first orientation with respect to the elongate fastening member with the fastener rotated 180° compared to FIG. 6.

Fastener 112 is provided with first and second ends 120, 122. As shown in FIG. 6, first end 120 is the leading end and second end 122 is the trailing end. In this position, when fastener 112 is pivoted to a second orientation, like distal fastener 106 of FIG. 1, tissue contacting surface 116 is in contact with the tissue. As shown in FIGS. 7 and 8, second end 122 is the leading end and first end 120 is the trailing end. In this position, when fastener 112 is pivoted to the second orientation, like proximal fastener 108 of FIG. 1, tissue contacting surface 116 is in contact with the tissue.

Fastener body 114 has a free surface 124 opposite tissue contacting surface 116. Free surface 124 is provided with a channel 126 that receives a portion of elongate fastening member 110 when fastener 112 is in a first orientation with respect to elongate fastening member 110. As shown in FIGS. 7 and 8, fastener 112 is being slid along elongate fastening member 110. In particular, a through bore 128 extends from tissue contacting surface 116 through free surface 124. Through bore 128 is larger in diameter than elongate fastening member 110 so that fastener 112 freely slides along elongate fastening member 110. A portion of elongate fastening member 110 fits within channel 126 on free surface 124 and a portion of elongate fastening member 110 fits within groove 118 on tissue contacting surface 116.

Fastener body 114 is shown with first end 120 having a substantially flat profile and second end 122 having a tapered profile. In general, any suitable external configuration can be used for fastener 112. Examples of fasteners may be found in U.S. Pat. Nos. 5,163,960; 5,403,348; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; and 10/797,685. The above cited patents and patent applications are hereby incorporated by reference.

Fastener 112 can be made of any biocompatible material suitable for a given application. For example, the fasteners may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, multi-component, solid, hollow, polygon-shaped, pointed, self-introducing, and combinations thereof. Also, the fasteners may include metallic material, polymeric material, ceramic material, composite material, body tissue, synthetic tissue, hydrophilic material, expandable material, compressible material, heat bondable material, and combinations thereof. Examples of body tissue include bone, collagen, cartilage, ligaments, or tissue graft material like xenograft, allograft, and autograft. The fasteners may also be made from a porous matrix or mesh of biocompatible and bioresorbable fibers acting as a scaffold to regenerate tissue.

The fasteners may further be made of or have a coating made of an expandable material. The material could be compressed then allowed to expand. Alternatively, the material could be hydrophilic and expand when it comes in contact with liquid. Examples of such expandable materials are ePTFE and desiccated body tissue.

Moreover, the fasteners described herein and incorporated by reference may include therapeutic substances to promote healing. These substances could include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

FIG. 9A shows an exemplary embodiment of an elongate fastening member 130. Elongate fastening member 130 includes a body 132 and has a stop 134 at a distal end. Body 132 can be selected for a given application. For example, if a rigid elongate fastening member 130 is needed, body 132 can be a rod or a tube. If a more flexible elongate fastening member 130 is needed, body 132 can be a suture. In general, a wire analogous to those used for cerclage of bone fractures is believed to provide a suitable combination of strength and flexibility. Although body 132 is shown as a single strand wire, the invention can be used with any type of surgical cable, such as a multi-strand cable.

Stop 134 can be made integral with body 132 or separate and then attached. Stop 134 is larger in diameter than through bore 128 in body 114 of fastener 112. Thus, once stop 134 reaches through bore 128, fastener 112 cannot be slid any further along elongate fastening member 130. As shown in FIG. 5, free surface 124 of fastener 112 is provided with a well 136 surrounding through bore 128. Well 136 is configured and dimensioned to receive at least a portion of stop 134. As shown in FIG. 10, this helps reduce the profile of the assembly when fastener 112 is in a second orientation with respect to elongate fastening member 130.

Referring to FIG. 9B, in another embodiment, the elongated fastener member 130 includes expandable members 131, positioned along the body 132. Upon insertion into the tissue, the expandable members 131 expand to engage the surrounding tissue. For examples, the expandable members 131 can be barbs. The barbs 131 engage the surrounding tissue, maintaining the elongated fastener member's 130 position within the tissue.

The elongate fastening members of the present invention may be made of metallic material, non-metallic material, composite material, ceramic material, polymeric material, co polymeric material, or combinations thereof. The members may be degradable, biodegradable, bioabsorbable, or nonbiodegradable. Examples of suture materials that can be used for the elongate fastening members are polyethylene, polyester, cat gut, silk, nylon, polypropylene, linen, cotton, and copolymers of glycolic and lactic acid. Preferably, the members are flexible or bendable. They may be threadlike, monofilament, multifilament, braided, or interlaced. The members may have a coating of therapeutic substances or drugs. For example, the members may include antibiotics, hydroxyapatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Figure 11:
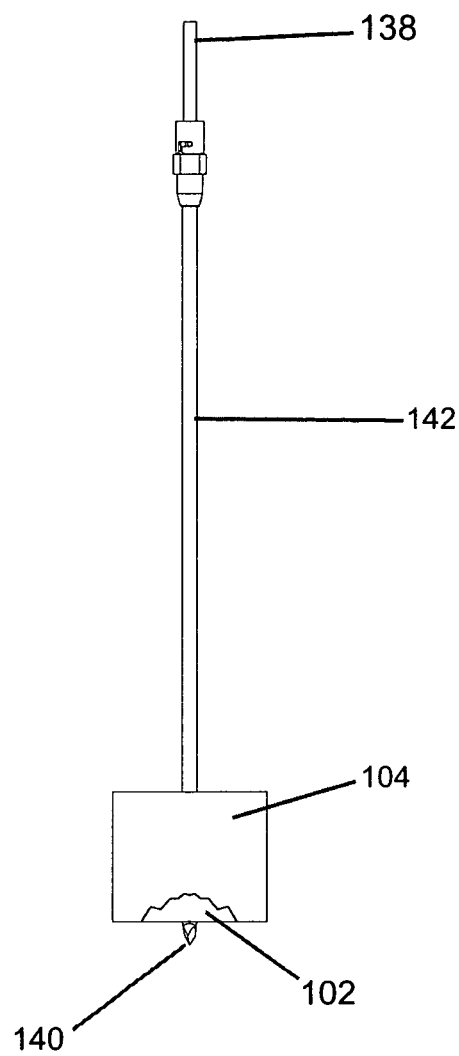
FIG. 11 shows a cannulated drill system used to create a passage through the tissue to be fixed.

The use of the tissue fixation system according to the present invention will now be described using fracture fixation as an example. If necessary, the fracture is reduced bringing fracture portion 102 into contact with bone 104 (FIG. 11). The reduction can be achieved using any number of techniques.

Figure 12:
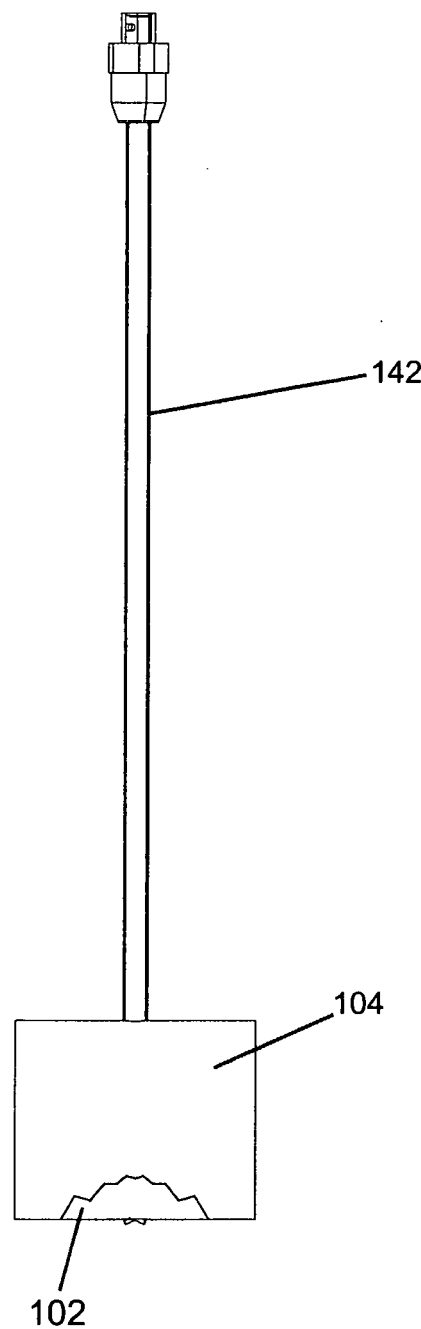
FIG. 12 shows a sleeve having a lumen through which the fixation system can be passed.

As also shown in FIG. 11, a drill system 138 is used to drill across the fracture, thereby creating a passage completely through bone 104. Drill system 138 includes a drill bit 140 with a headpiece configured for attachment to a drill. A stop can be placed on the headpiece and prevents drill bit 140 from penetrating too far beyond the tissue to be drilled. Drill system 138 may be a cannulated drill system that fits over a k-wire or other similar guide wire. A cannula or sleeve 142 may encircle drill bit 140 or at least the shaft portion of drill bit 140. As drill bit 140 creates a passage through bone 104, sleeve 142 is positioned in the passage. Drill system 138 is used to create a passage in bone 104 from the proximal side of bone 104 to the distal side of bone 104, then the drill and drill bit 140 are removed from sleeve 142 (FIG. 12).

Figure 13:
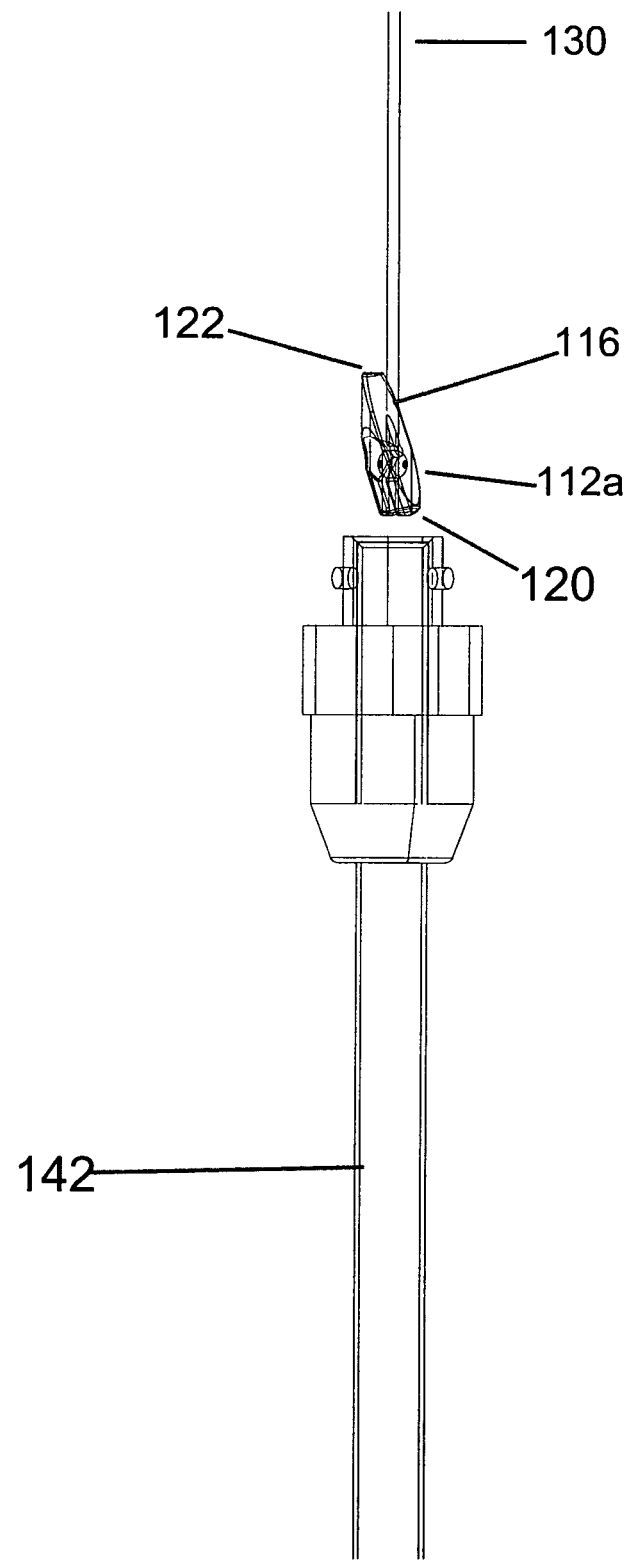
FIG. 13 shows a distal fastener being inserted into the sleeve.
Figure 14:
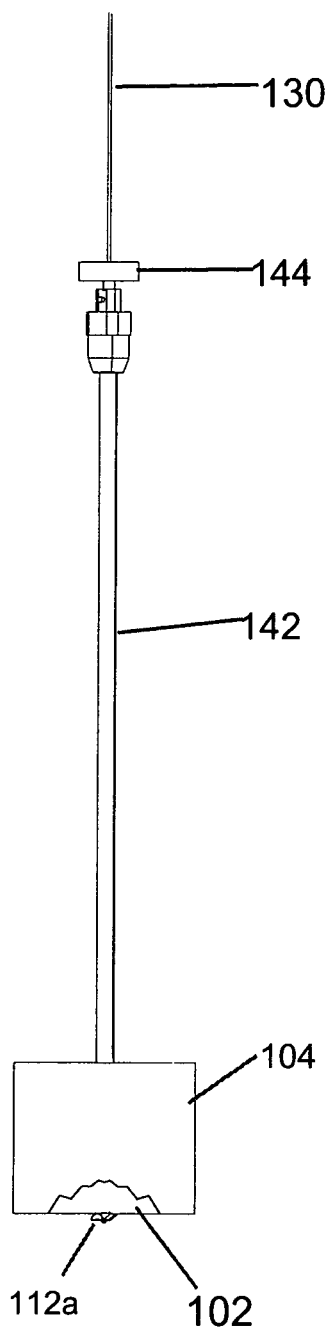
FIG. 14 shows a pushrod used to move the distal fastener through the sleeve.
Figure 15:
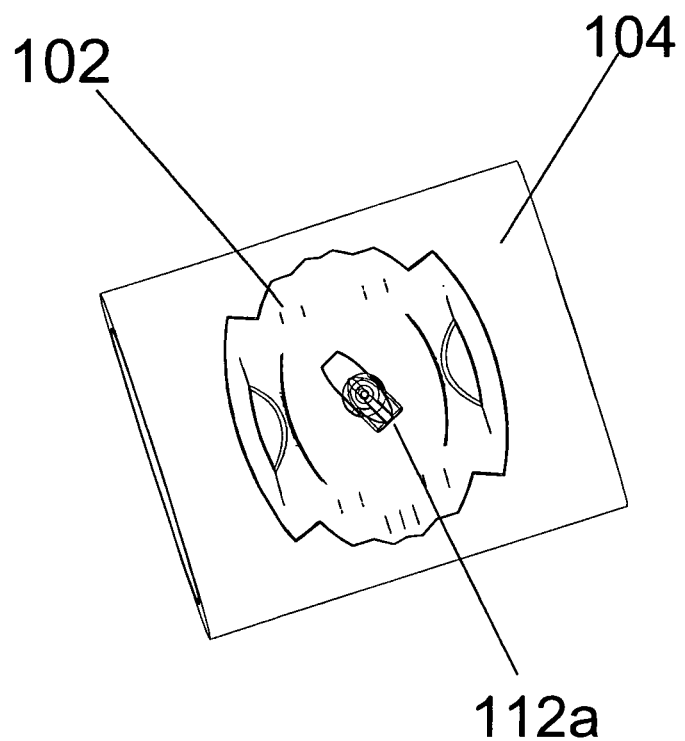
FIG. 15 shows the distal fastener in the second orientation.

As shown in FIG. 13, a distal fastener 112a is inserted into sleeve 142. Distal fastener 112a is inserted in the first orientation with respect to elongate fastening member 130 with first end 120 as the leading end. In this configuration, tissue contacting surface 116 will be in contact with fracture portion 102 when distal fastener 112a is pivoted into the second orientation. This is best seen in FIGS. 14 and 15, in which a pushrod 144 is used to advance distal fastener 112a and elongate fastening member 130 through sleeve 142. Pushrod 144 also facilitates the pivoting of distal fastener 112a from the first orientation to the second orientation. This pivoting is not possible until distal fastener 112a has exited through sleeve 142. Also, since the length of distal fastener 112a is larger than the passage created in bone 104, pulling back on elongate fastening member 130 helps to ensure distal fastener 112a is in the second orientation and flush against fracture portion 102.

Figure 16:
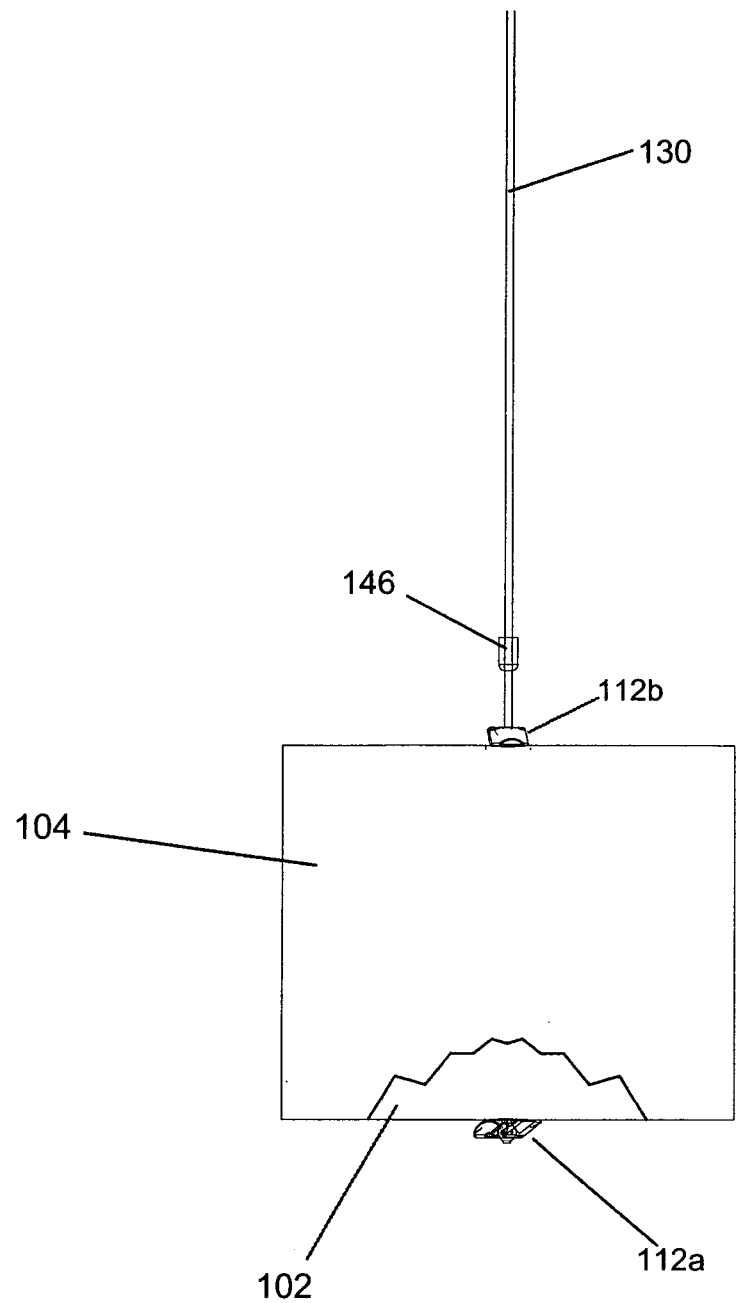
FIG. 16 shows a proximal fastener being used to maintain the tension in the elongate fastening member.

As illustrated in FIG. 16, sleeve 142 is removed from bone 104. Fastener 112a is located on the distal side of bone 104. Elongate fastening member 130 extends from fastener 112a through the bone passage and out the proximal opening of the bone or tissue passage. Any suitable means can be used to keep distal fastener 112a against fracture portion 102 with tension, where the tension can be measure and controlled in accordance with use. For example, elongate fastening member 130 can be deformed at the proximal end of the passage such that the deformed section rests against bone 104. The deformation would depend on the nature of elongate fastening member 130. If elongate fastening member 130 is a relatively flexible element, such as a suture, cable, or wire, then simply tying a knot in fastening member 130 could be sufficient to maintain the tension. If elongate fastening member 130 does not allow a knot, such as would be the case with a rod or tube, then mechanical deformation of elongate fastening member 130 to create an enlarged head could be sufficient to maintain the tension. U.S. Patent Application Publication No. US 2002/0016593, the contents of which are incorporated herein by reference, discloses mechanisms to mechanically deform an extension member and could be used to deform elongate fastening member 130.

Alternatively, the elongated fastening member 130 can be deformed by an energy, such as thermal energy, to deform elongate fastening member 130 to create an enlarged head sufficient to maintain the tension.

In an exemplary embodiment, a proximal fastener 112b is used to secure distal fastener 112a and elongate fastening member 130. In this embodiment, proximal fastener 112b is identical to distal fastener 112a. If not already pre-loaded, proximal fastener 112b is loaded onto elongate fastening member 130. Proximal fastener 112b is loaded as shown in FIGS. 7 and 8, i.e. with second end 122 as the leading end so that after proximal fastener 112b is slid down against bone 104 and pivoted into the second orientation, tissue contacting surface 116 is in contact with bone 104.

Elongate fastening member 130 is tensioned, and proximal fastener 112b is secured to elongate fastening member 130 to thereby approximate the fracture and stabilize bone 104. The tension of elongate fastening member 130 pulls on distal and proximal fasteners 112a, 112b generally toward each other, thereby applying pressure to the fractured bone or tissue. In this regard, a bushing 146 can be used to secure proximal fastener 112b with the desired tension. Single or multiple elongated members 130 can be used to secure the fractured bone or tissue.

Although a number of mechanisms can be used to secure bushing 146, an instrument or medical device particularly useful for this will now be described.

In this regard, the present invention also provides a medical device for securing a fastener against relative movement with respect to a cable. As previously disclosed, a cable and pair of oppositely spaced fasteners can be used to secure a bone facture. The cable is passed through the bone and fracture; a first fastener secures the cable on a first side (fracture side) of the bone; and a second fastener is positioned about the cable on a second side of the bone, opposite the first fastener. A bushing is positioned onto the cable to secure the second fastener against the second side of the bone. A force is applied to the bushing, compressing the second fastener against the second side of the bone and providing a tension to the cable. The tension in the cable can be measured and controlled, for example, with the used of a sensor and spring element. The spring can apply the force to tension the cable, and the sensor can be used to measure the resulting tension. Alternatively, the sensor can measure the compression of the tissue to determine the tension. The bushing is crimped about the cable, securing the second fastener against the second side of the bone, such that a tension is provided through the cable between the first and second fasteners.

Figure 17:
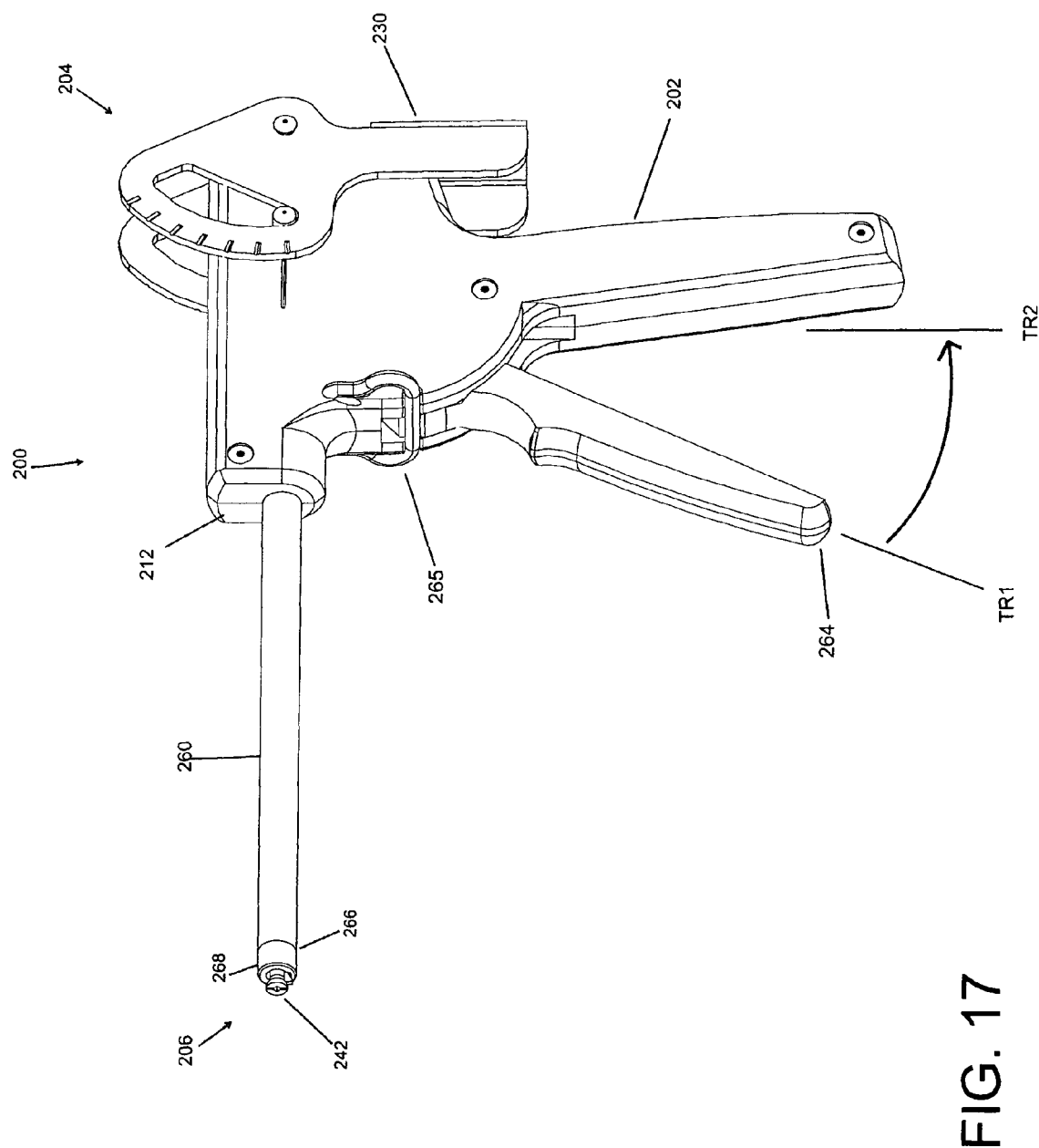
FIG. 17 depicts a front isometric view of the medical device of the present invention.

Referring to FIG. 17, a medical device 200 is provided for securing the bushing to the cable. The medical device 200 includes a handle portion 202 having a tensioning mechanism 204, tensioning the cable and applying a force to the bushing, and a crimping mechanism 206 for securing the bushing to the cable.

Figure 18:
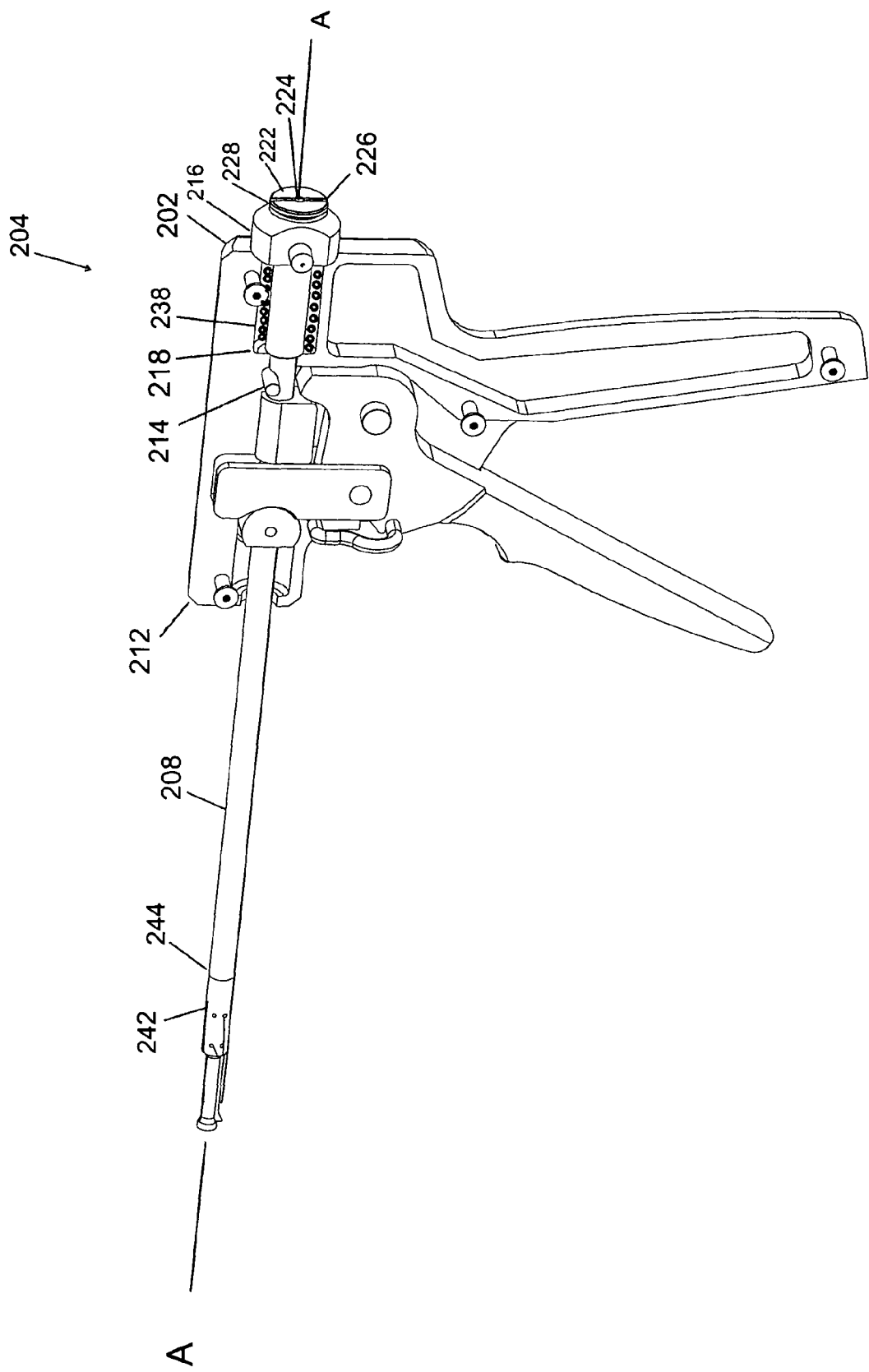
FIG. 18 depicts a rear partial isometric view showing the tensioning mechanism of the medical device of FIG. 17.
Figure 19:
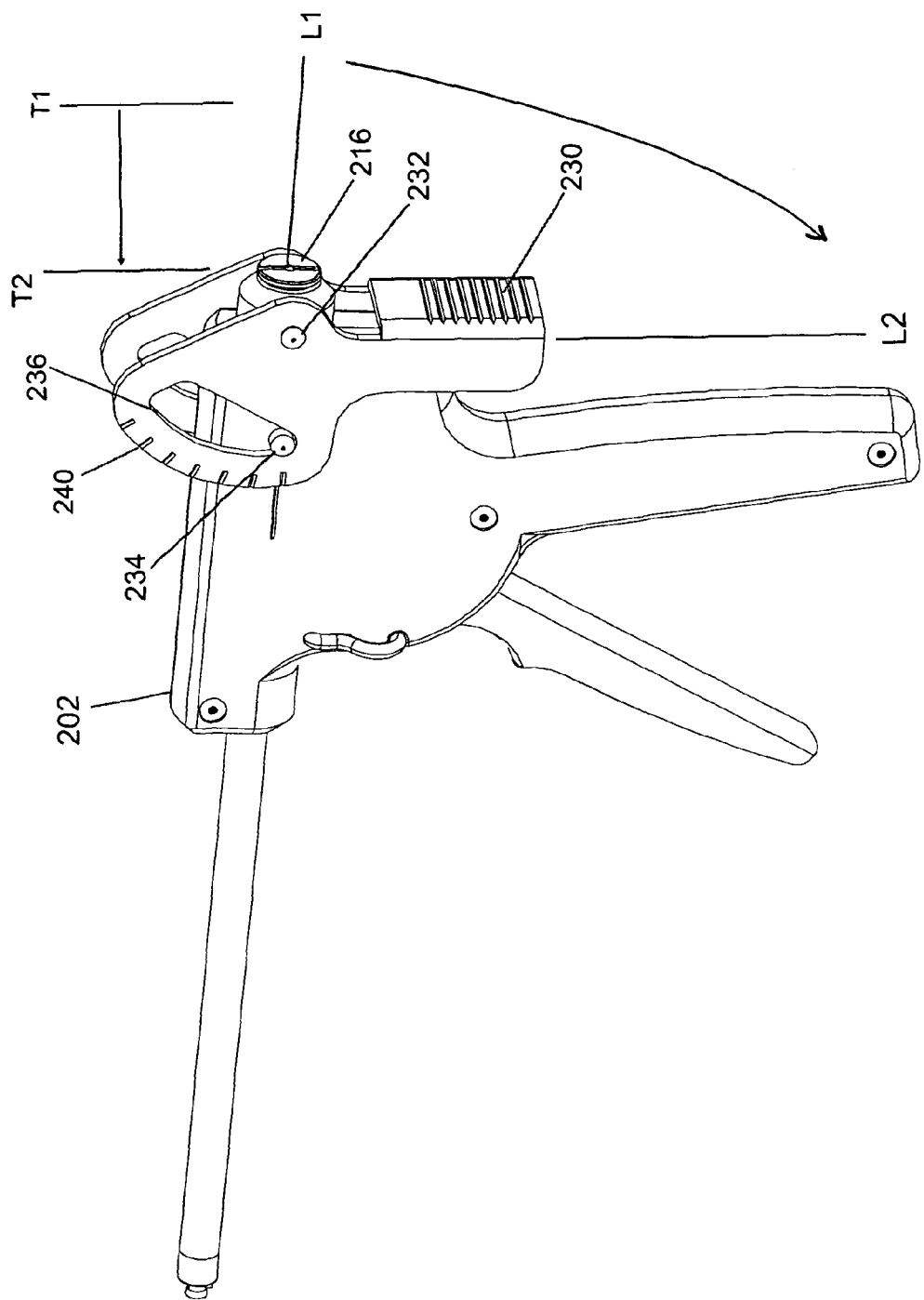
FIG. 19 depicts a rear isometric view showing the tensioning mechanism of the medical device of FIG. 17.

Referring also to FIGS. 18 and 19, the tensioning mechanism 204 includes a collett holder 208 defining a longitudinal passage along a central longitudinal axis A. The collett holder 208 is affixedly positioned through a top portion 212 of the handle portion 202 with collett holder pin 214. A cable tensioner 216 is slidably positioned on a first end 218 of the collett holder 208. The cable tensioner 216 defines a cable passage longitudinally aligned with the longitudinal passage of the collett holder 208. An end portion 222 of the cable tensioner 216 includes a cable aperture 224 for threading the cable there through. A radial groove 226 and circumferential groove 228 are provided on the end portion 222 of the cable tensioner 216, such that the cable can be wrapped about the circumferential groove 228 of the cable tensioner 216, thereby preventing relative movement between the cable and the cable tensioner 216.

A cable tension lever 230 is pivotally connected to the cable tensioner 216 with a lever pin 232. The cable tension lever 230 is adjustably positioned on the handle portion 202 with body pins 234, wherein a body pin 234 is mirrorly positioned on opposite sides of the handle portion 202. The body pins 234 are engaged in the cable tension lever 230 arcuate lever slots 236, such that cable tension lever 230 and cable tensioner 216 are movably connected to the handle portion 202.

In use, as the cable tension lever 230 is pivoted about the cable tensioner 216 from a first lever position L1 to a second lever position L2, the body pins 234 traverse the arcuate lever slots 236, resulting in a translation of the cable tensioner 216 along the first end 218 of the collett holder 208 from a first tensioner position T1 to a second tensioner position T2. A tension bias member 238 is interposed between the cable tensioner 216 and the handle portion 202, biasing the cable tensioner 216 into the first tensioner position T1. The cable tension lever 230 includes tension indicating markings 240 along each of the arcuate lever slots 236. The tension markings 240 indicate the tension to be applied to the cable.

Figure 34:
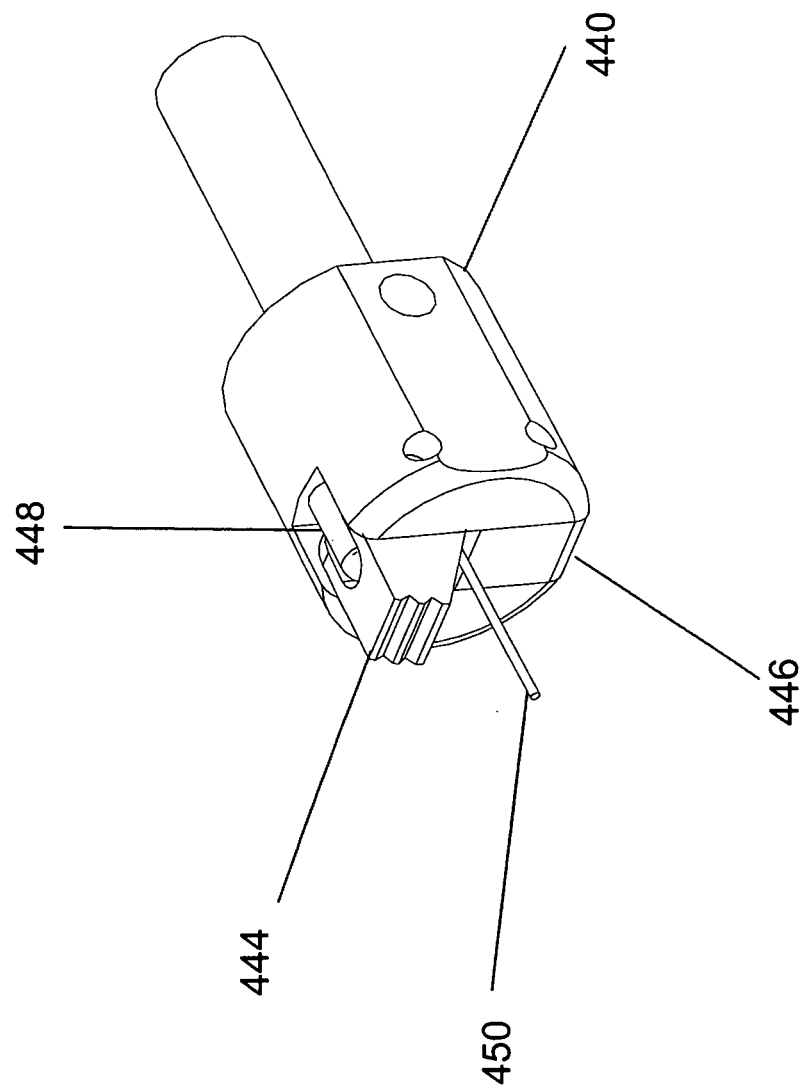
FIG. 34 depicts an alternative cable tensioner for the medical device of FIG. 17.
Figure 35:
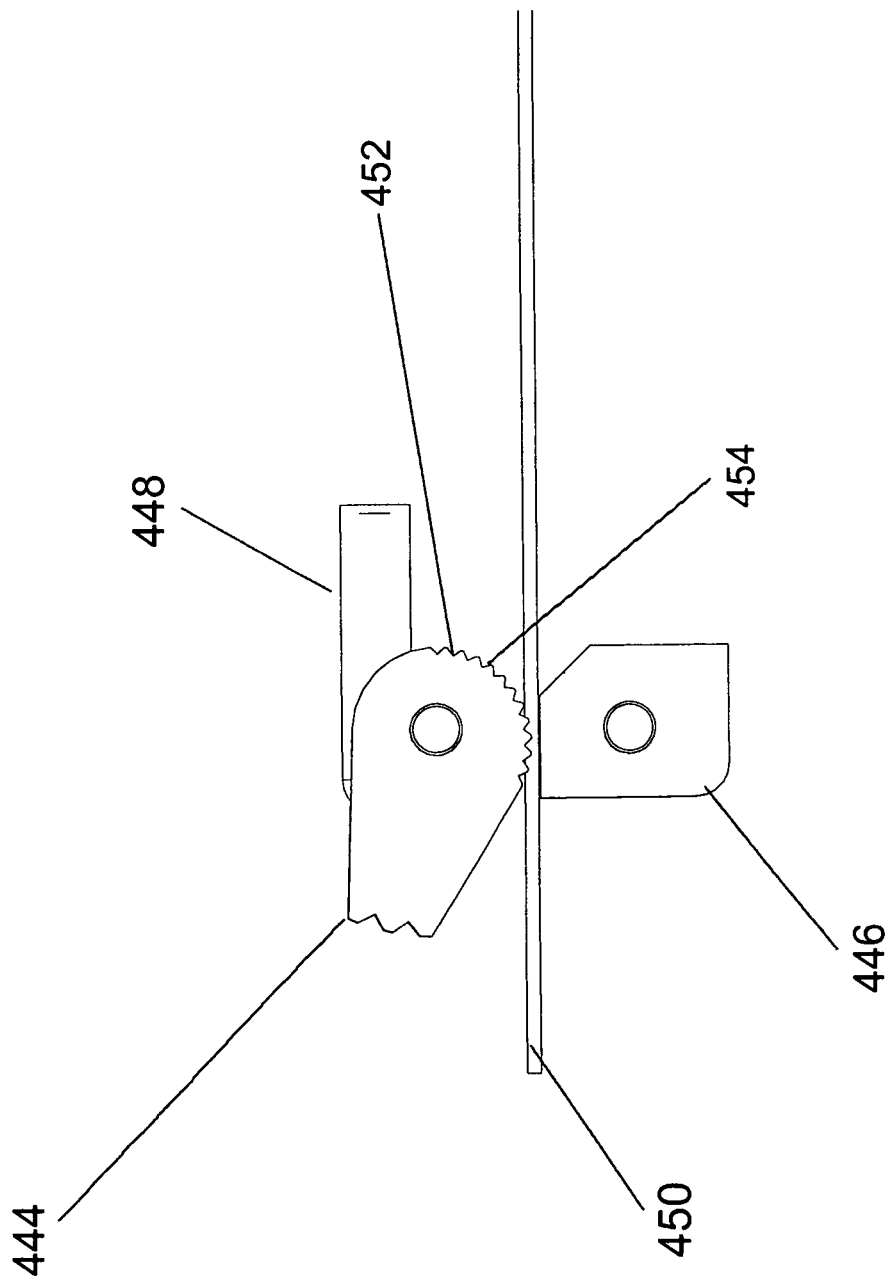
FIG. 35 depicts a sectional view of the cable tensioner of FIG. 34.

Referring also to FIG. 34 an alternative cable tensioner 440 is provided. Cable tensioner 440 is slidably positioned on a first end 218 of the collett holder 208. The cable tensioner 440 defines a cable passage longitudinally aligned with the longitudinal passage of the collett holder 208. An end portion 442 of the cable tensioner 440 includes a cleat 444 and a cleat stop 446. The cleat 444 is pivotally mounted to the cable tensioner 440, including a bias member 448 biasing the cleat 444 into a closed position. A cable 450 is threadable between the cleat 446 and the cleat stop 448, where in the closed position the cleat 446 imparts a force onto the cable 450, securing the cable 450 in the cable tensioner 440.

The bias member 448 biases the cleat 444 such that in the closed position the cable can be further drawn through the cable tensioner 440, for example, to position the fastener proximal to the tissue while removing any initial slack from the cable 450. However, the cleat 444 prevents the cable 450 from being drawn back through the cable tensioner 440. For example, the cleat 444 can include an arcuate contact surface 452 such that the force imparted on the cable 450 in the closed position increases as the tension on the cable 450 increases, preventing the cable 450 from being drawn back through the cable tensioner 440. The cleat arcuate surface 452 can further include a plurality of teeth 454, which can be utilized to grip cable 450.

Figure 20:
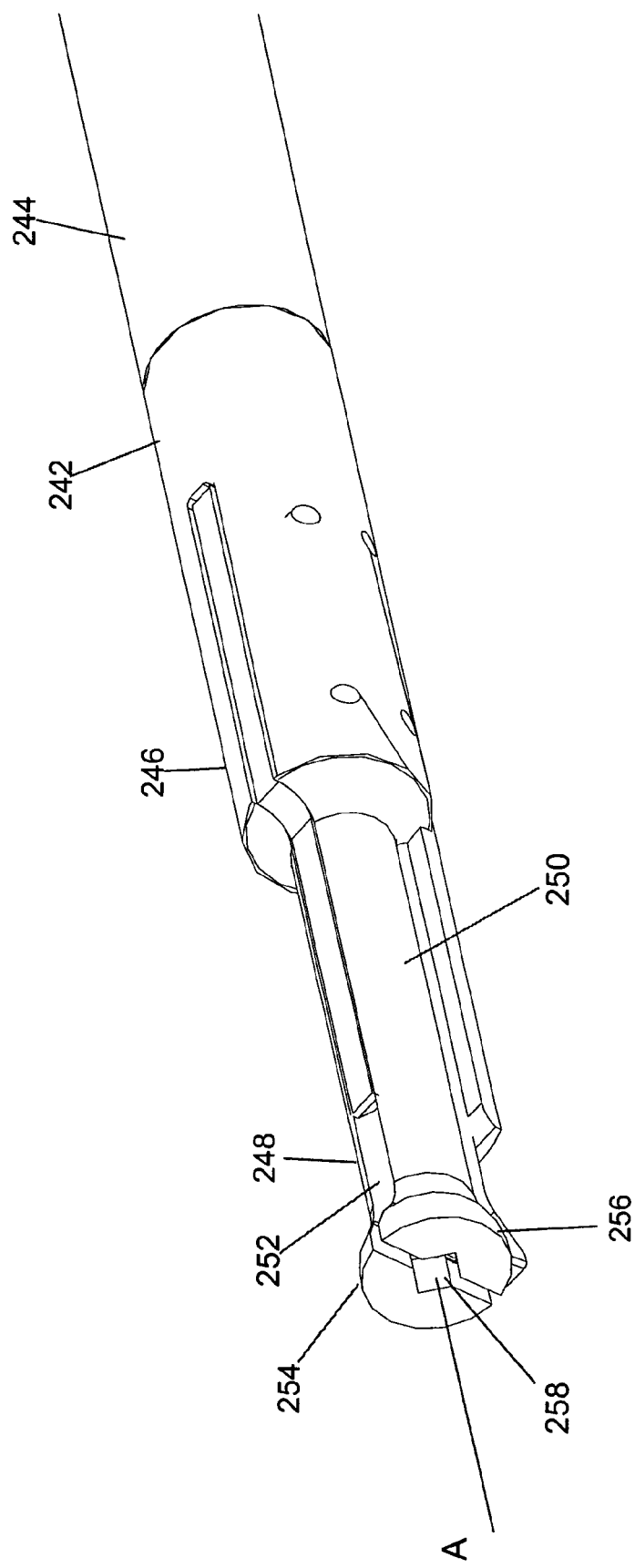
FIG. 20 depicts an isometric view of the crimping mechanism collett of the medical device of FIG. 17.

Referring to FIGS. 18 and 20, a collett 242 is affixed to a second end portion 244 of the collett holder 208, opposite the cable tensioner 216. The collett 242 defines a collett passage longitudinally aligned with the longitudinal passage of the collett holder 208 along the central longitudinal axis A. An end portion of the collett 242 is bisected, forming first and second collett arms 248 and 250. A gap portion 252 is provided between the first and second collett arms 248 and 250. Each of the first and second collett arms 248 and 250 includes force application end portions 254 and 256. The force application end portions 254 and 256 combine to form a bushing aperture 258 configured to received the bushing therein. The collett 242 is made of a semi-rigid material, such that the first and second collett arms 248 and 250 can be moved from an open to a closed position, closing the gap 252 between the force application end portions 254 and 256.

In use, the tensioning mechanism 204 is used to tension the cable. The cable can include a single or multiple filaments. The cable is inserted through the medical device 200 along the central longitudinal axis A, through the collett 242, collett holder 208, and the cable tensioner 216, positioning the bushing in the bushing aperture 258 and extending the cable through the cable aperture 224. To tension the cable, the cable tension lever 230 is actuated from the first lever position L1 to the second lever position L2, sliding the cable tensioner 216 along the collett holder 208 from the first tensioner position T1, into the handle portion 202 against the tension bias member 238, to the second tensioner position T2. The cable is positioned through the radial groove 226 and wrapped about the circumferential groove 228 on the end portion 222 of the cable tensioner 216, securing the cable to the cable tensioner 216. The cable tension lever 230 is released, such that tension bias member 238 biases the cable tensioner 216 from the second tensioner position T2 towards the first tensioner position T1. The movement of the cable tensioner 216 towards the first tensioner position T1 applies a tension to the cable, forcing the bushing into the second fastener. The applied tension can be selected by actuating the cable tension lever 230 to the desired tension marking 240.

Figure 21:
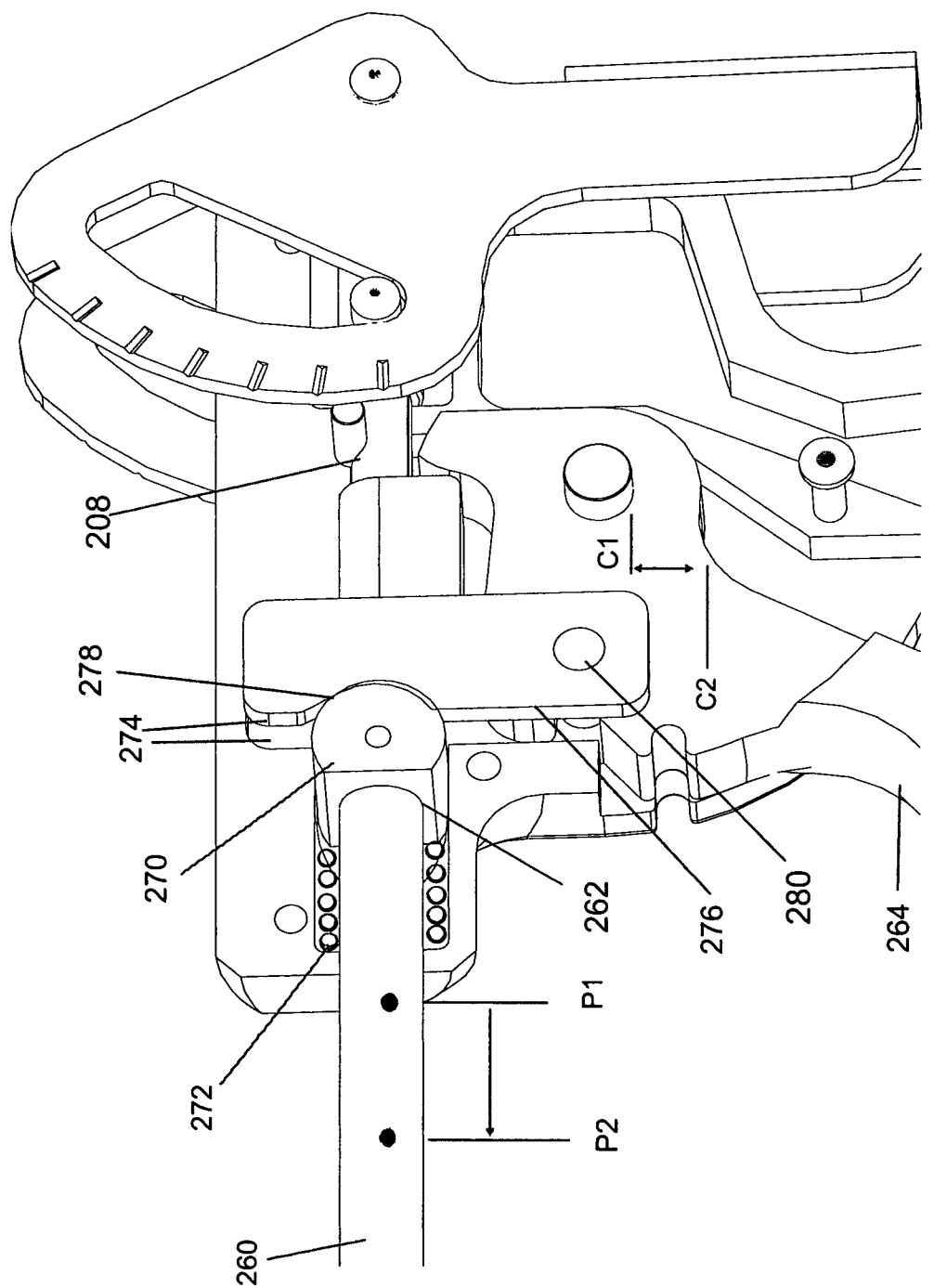
FIG. 21 depicts a partial isometric view showing the handle portion of the crimping mechanism of the medical device of FIG. 17.

Referring again to FIGS. 17 and 21, the crimping mechanism 206 includes an outer tube 260 slidingly positioned over the collett holder 208. The outer tube 260 includes a first end 262 operably connected to a trigger 264 and a second end 266 connected to a collett closer 268. The trigger 264 is pivotally mounted in the handle portion 202, such that the trigger 264 can be actuated from a first trigger position TR1 to a second trigger position TR2. A locking mechanism 265 prevents the trigger 264 from being actuated. The locking mechanism 265 is rotated to disengage the trigger 264, allowing actuation of the trigger 264.

The operable connection between the first end of the outer tube 262 and the trigger 264 includes an outer tube ferrule 270 slidably positioned about the collett holder 208 and affixed to the first end of the outer tube 262. A tube bias member 272 is interposed between the handle portion 202 and the outer tube ferrule 270, such that the tube bias member 272 biases the outer tube ferrule 270 and the outer tube 260 into a first tube position P1. A pair of crimp cams 274 are pivotally connected to the handle portion 202 on opposite sides of the trigger 264. The crimp cams 274 each include first edges 276 having an arcuate section 278 for engaging the outer tube ferrule 270, where the crimp cams 274 are translatable with respect to the handle portion 202 from a first cam position C1 to a second cam position C2.

An actuation of the trigger 264 from a first trigger position TR1 to a second trigger position TR2 translated the crimp cams 274 with respect to the handle portion from a first cam position C1 to a second cam position C2 position. The arcuate sections 278 of the crimp cams 274 engage the outer tube ferrule 270, translating the outer tube ferrule 270 and the outer tube 260 along the collett holder 208 from the first tube position P1 to a second tube position P2. As the trigger 264 is released, the tube bias member 272 biases the outer tube ferrule 270 and the outer tube 260 from the second tube position P2 to the first tube position P1. Simultaneously, the crimp cams 274 and the trigger 264 are moved to the first cam position C1 and the first trigger position TR1.

Figure 22:
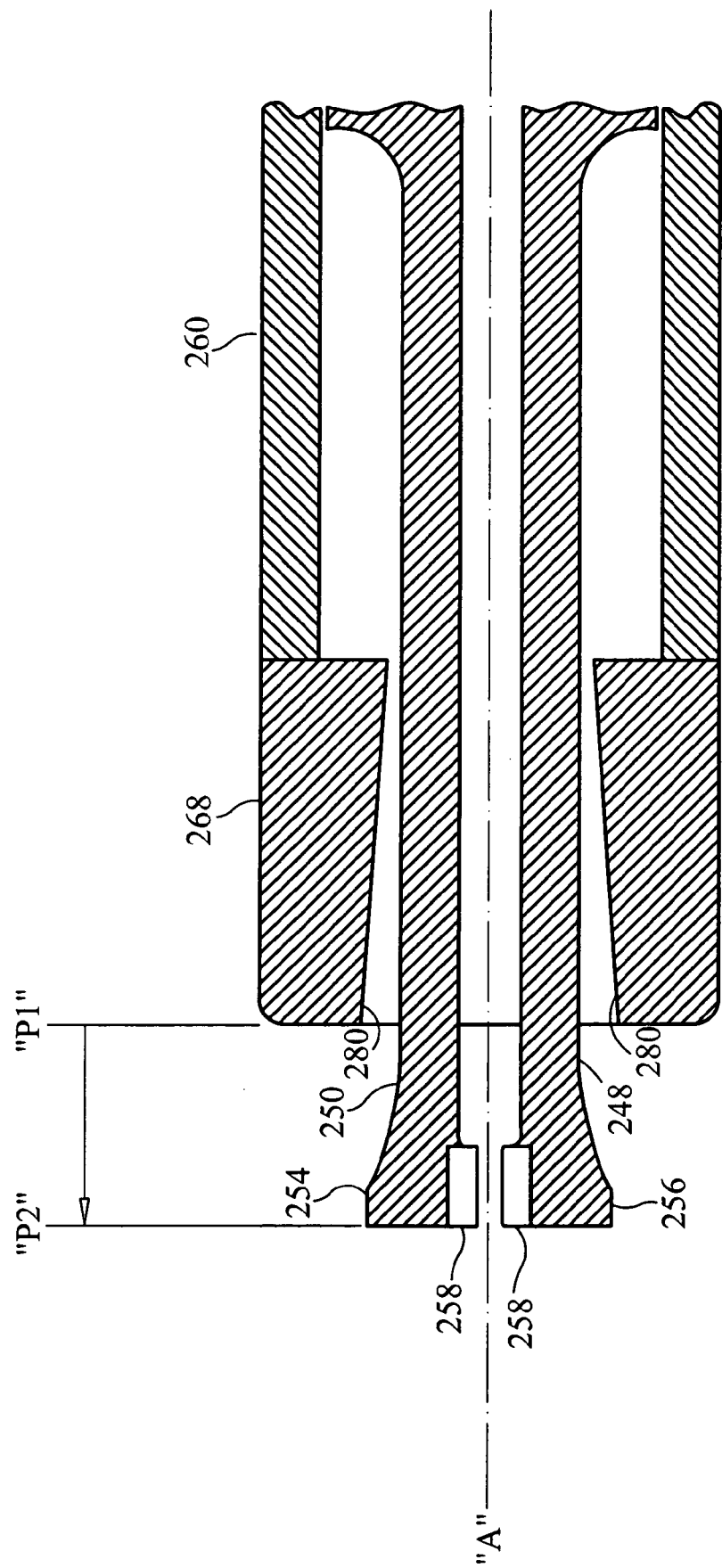
FIG. 22 depicts a top sectional view of the crimping mechanism collett closer of the medical device of FIG. 17.

Referring to FIGS. 17 and 22, the collett closer 268 is positioned on the outer tube 260 proximal to the force application end portions 254 and 256 of the first and second collett arms 248 and 250. As the outer tube 260 is moved from the first tube position P1 to the second tube position P2, the collett closer 268 is moved over the force application end portions 254 and 256. The collett closer 268 includes inner tapered surfaces 280, such that the inner tapered surfaces 280 apply compressive forces to the force application end portions 254 and 256 as the collett closer 268 is moved over the force application end portions 254 and 256, closing the gap 252 there between.

In use, the trigger 264 is actuated from the first trigger position TR1 to the second trigger position TR2. The actuation of the trigger 264 slides the outer tube 260 along the collett holder 208 from the first tube position P1 to the second tube position P2, moving collett closer 268 about the force application end portions 254 and 256 of the first and second collett arms 248 and 250. The inner tapered surfaces 280 of the collett closer 268 apply compressive forces to the first and second force application end portions 254 and 256, closing the gap 252 there between. The trigger 264 is released, allowing the tube bias member 272 to bias the outer tube 260 from the second tube position P2 to the first tube position P1, moving the collett closer 268 from the force application end portions 254 and 256.

Figure 23:
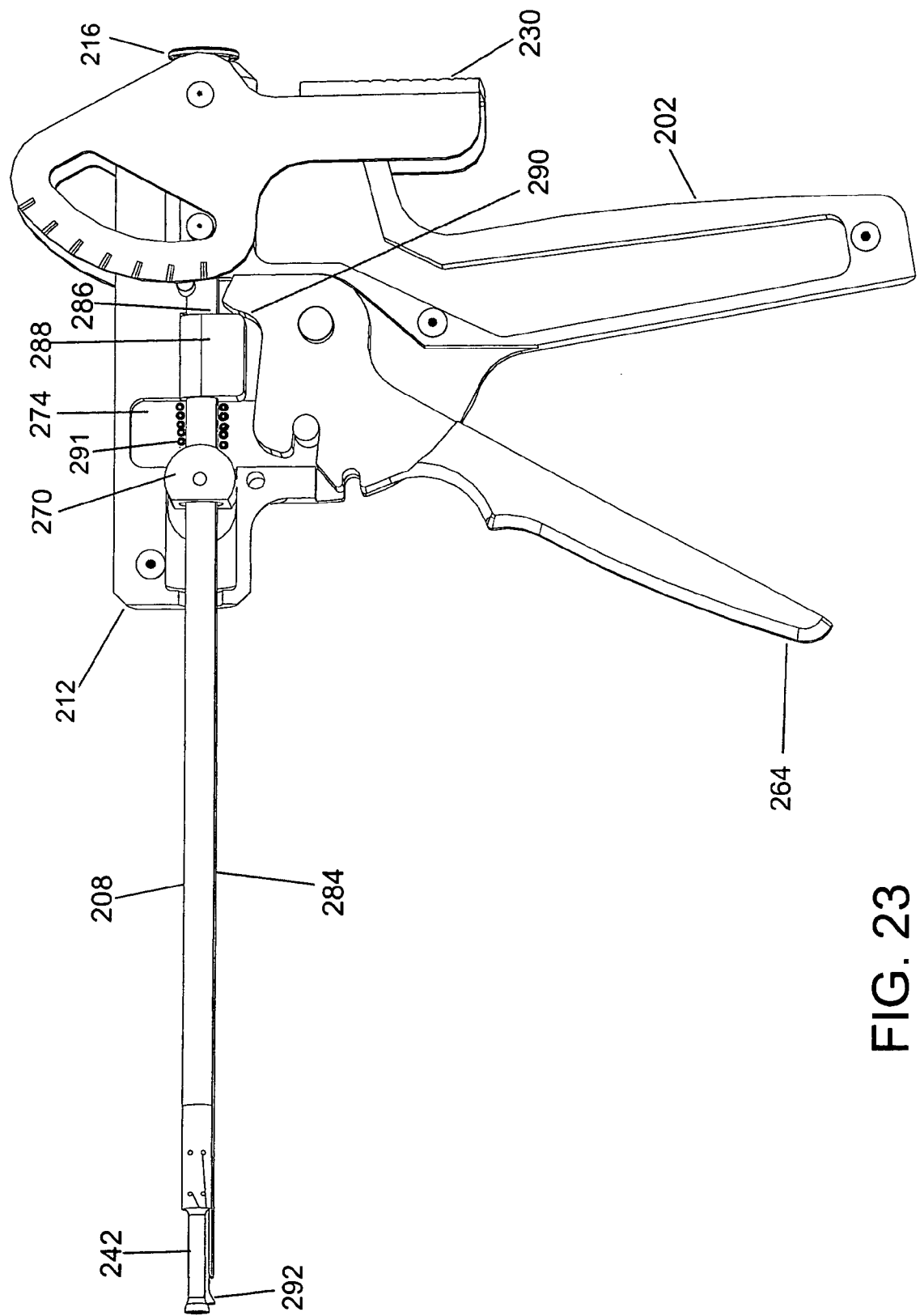
FIG. 23 depicts a partial isometric view showing the cutting mechanism of the medical device of FIG. 17.
Figure 24:
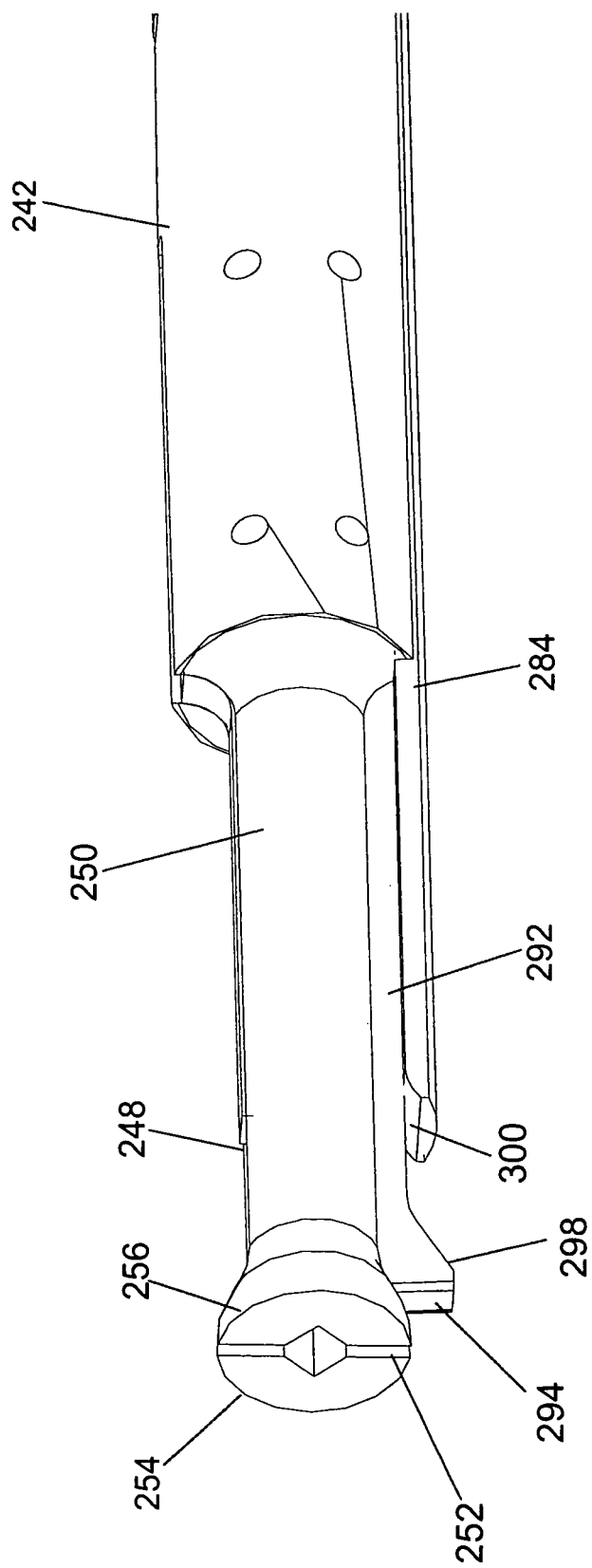
FIG. 24 depicts a partial isometric view showing the collett portion of the cutting mechanism of FIG. 23.
Figure 25:
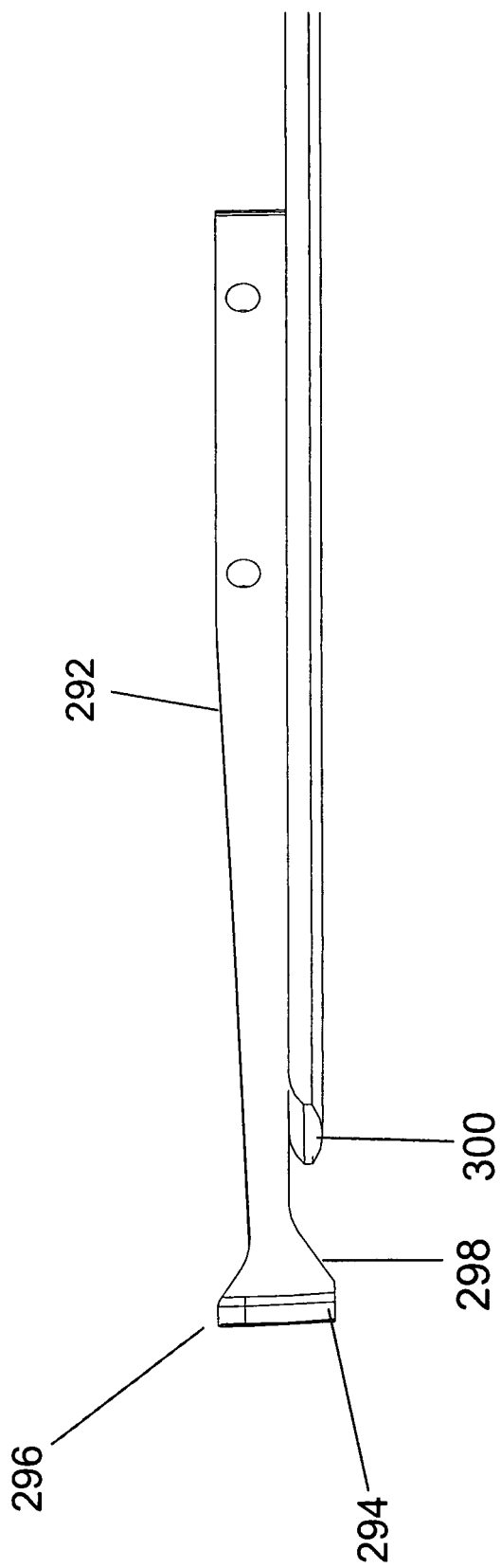
FIG. 25 depicts an isometric view showing the cutting arm of the cutting mechanism of FIG. 24.

Referring to FIGS. 23-25, the crimping mechanism 206 can further include a cutting mechanism. The cutting mechanism includes a cut off cam 284 slidingly positioned along a bottom portion of the collett holder 208. The cut off cam 284 includes a first end portion 286 positioned through the outer tube ferrule 270. A cut off cam ring 288 is slidably positioned about the collett holder 208, engaging the first end portion 286 of the cut off cam 284. The cut off cam ring 288 is positioned proximal to the trigger 264, such that as the trigger 264 is actuated from the first trigger 264 position TR1 to the second trigger 264 position TR2, a top portion 290 of the trigger 264 engages the cut off cam ring 288, sliding the cut off cam ring 288 and cut off cam 284 along the collett holder 208. A cut off bias member 291 is interposed between the outer tube ferrule 270 and the cut off cam ring 288.

A cut off arm 292 is connected to the collett 242, at least partially positioned in the gap 252 between the first and second collett arms 248 and 250. The cut off arm 292 includes a cutting head portion 294 positioned proximal to the first and second force application end portions 254 and 256, at least partially positioned in the gap 252, interposed between the first and second collett arms 248 and 250. The cutting head portion 294 includes a cutting edge 296, for cutting the cable, and a lower angular surface 298 for engagement by a second end portion 300 of the cut off cam 284.

In use, the trigger 264 is actuation from the first trigger position TR1 to the second trigger position TR2. The actuation of the trigger 264 results in the top portion 290 of the trigger 264 engaging the cut off cam ring 288, sliding the cut off cam ring 288 and cut off cam 284 along the collett holder 208. The second end portion 300 of the cut off cam 284 engages the angular surface 298 of the cutting head 294, forcing the cutting edge 296 into the cable, cutting the cable. The trigger 264 is released, allowing the cut off bias member 291 to bias the cut off cam 284 from the cutting head 294.

Figure 26:
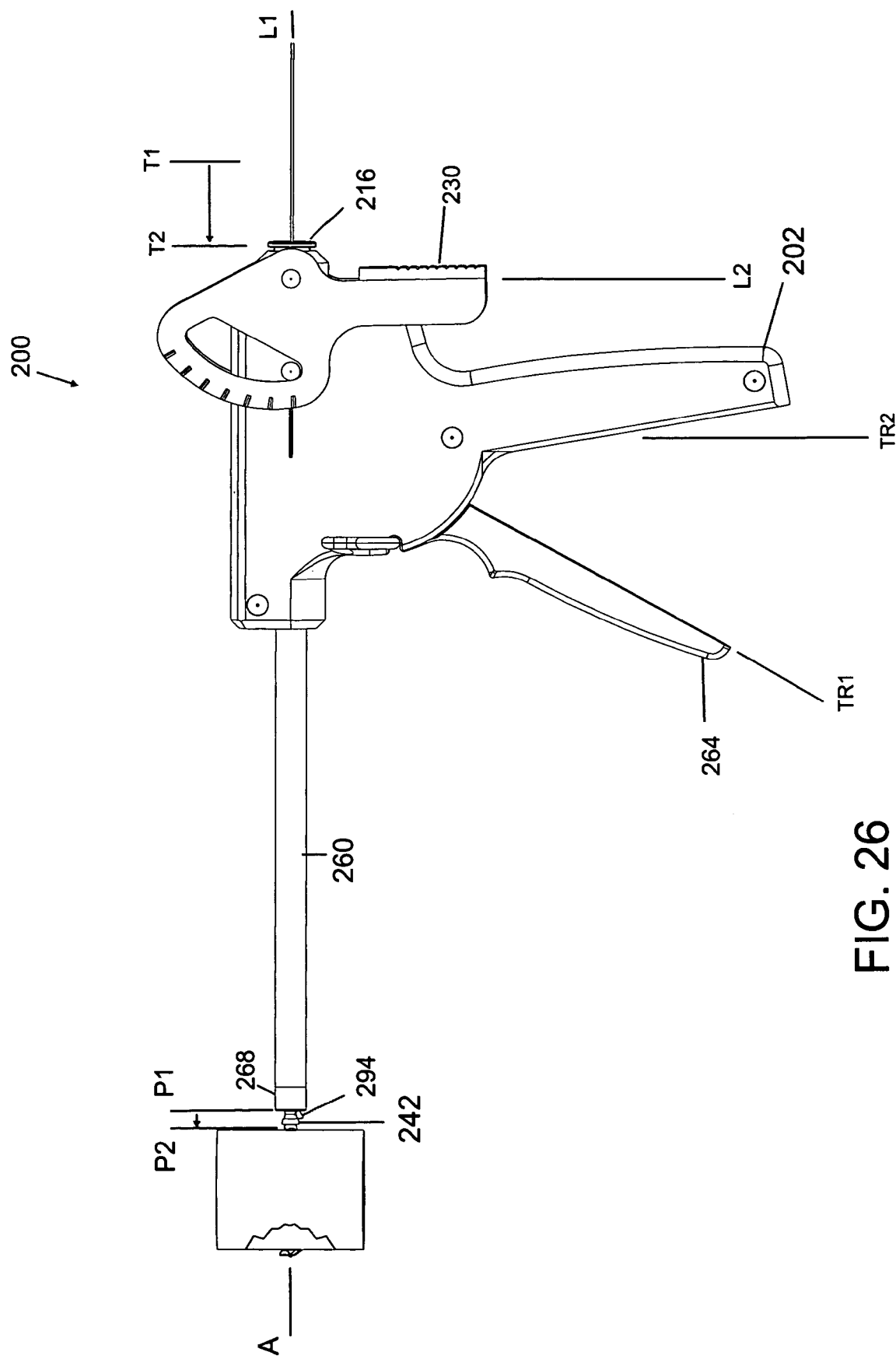
FIG. 26 depicts the medical device of FIG. 17 in use to secure a bone fracture.

Referring to FIG. 26, in a method of use, the cable is passed through the bone and fracture, where a first fastener secures the cable on a first side (fracture side) of the bone and a second fastener is positioned about the cable on a second side of the bone, opposite the first fastener. A bushing is positioned onto the cable to secure the second fastener against the second side of the bone.

The cable is inserted through the medical device 200 along the central longitudinal axis "A", through the collett 242, collett holder 208, and the cable tensioner 216, positioning the bushing in the bushing aperture 258 and extending the cable through the cable aperture 224. To tension the cable, the cable tension lever 230 is actuated from the first lever position L1 to the second lever position L2, sliding the cable tensioner 216 along the collett holder 208 from the first tensioner position T1, into the handle portion 202 against the tension bias member 238, to the second tensioner position T2. The cable is positioned through the radial groove 226 and wrapped about the circumferential groove 228 on the end portion 222 of the cable tensioner 216, securing the cable to the cable tensioner 216. The cable tension lever 230 is released, such that tension bias member 238 biases the cable tensioner 216 from the second tensioner position T2 towards the first tensioner position T1. The movement of the cable tensioner 216 towards the first tensioner position T1 applies a tension to the cable, pressing the bushing against the second fastener. The applied tension can be selected by actuating the cable tension lever 230 to the desired tension marking 240.

The trigger 264 is actuated from the first trigger position TR1 to the second trigger position TR2. The actuation of the trigger 264 slides the outer tube 260 along the collett holder 208 from the first tube position P1 to the second tube position P2, moving collett closer 268 about the force application end portions 254 and 256 of the first and second collett arms 248 and 250. The inner tapered surfaces 280 of the collett closer 268 apply compressive forces to the first and second force application end portions 254 and 256, compressing the first and second force application end portions 254 and 256 about the bushing positioned in the bushing aperture 258. The compressive forces crimp the bushing about the cable, securing the bushing to the cable.

Simultaneously, the actuation of the trigger 264 results in the top portion 290 of the trigger 264 engaging the cut off cam ring 288, sliding the cut off cam ring 288 and cut off cam 284 along the collett holder 208. The second end portion 300 of the cut off cam 284 engages the angular surface 298 of the cutting head 294, forcing the cutting edge 296 into the cable, cutting the cable.

In another embodiment a medical device 320 of the present invention secures a fastener against relative movement with respect to a suture, with the fastener itself being deformed. Medical device 320 is substantially similar to medical device 200 and like reference number shall be used to indicate like items.

Figure 27:
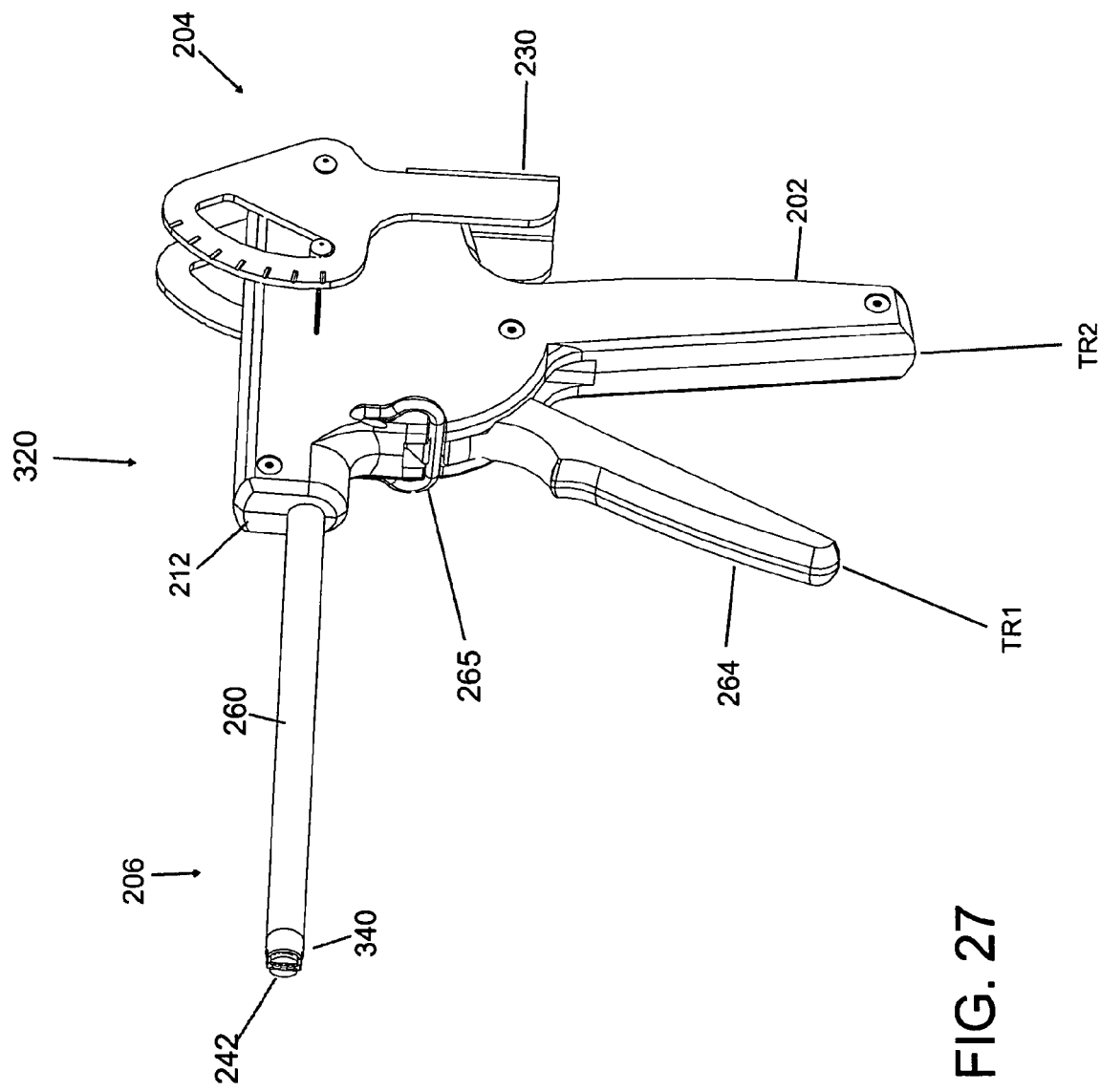
FIG. 27 depicts a front isometric view of an alternative medical device of the present invention.
Figure 28:
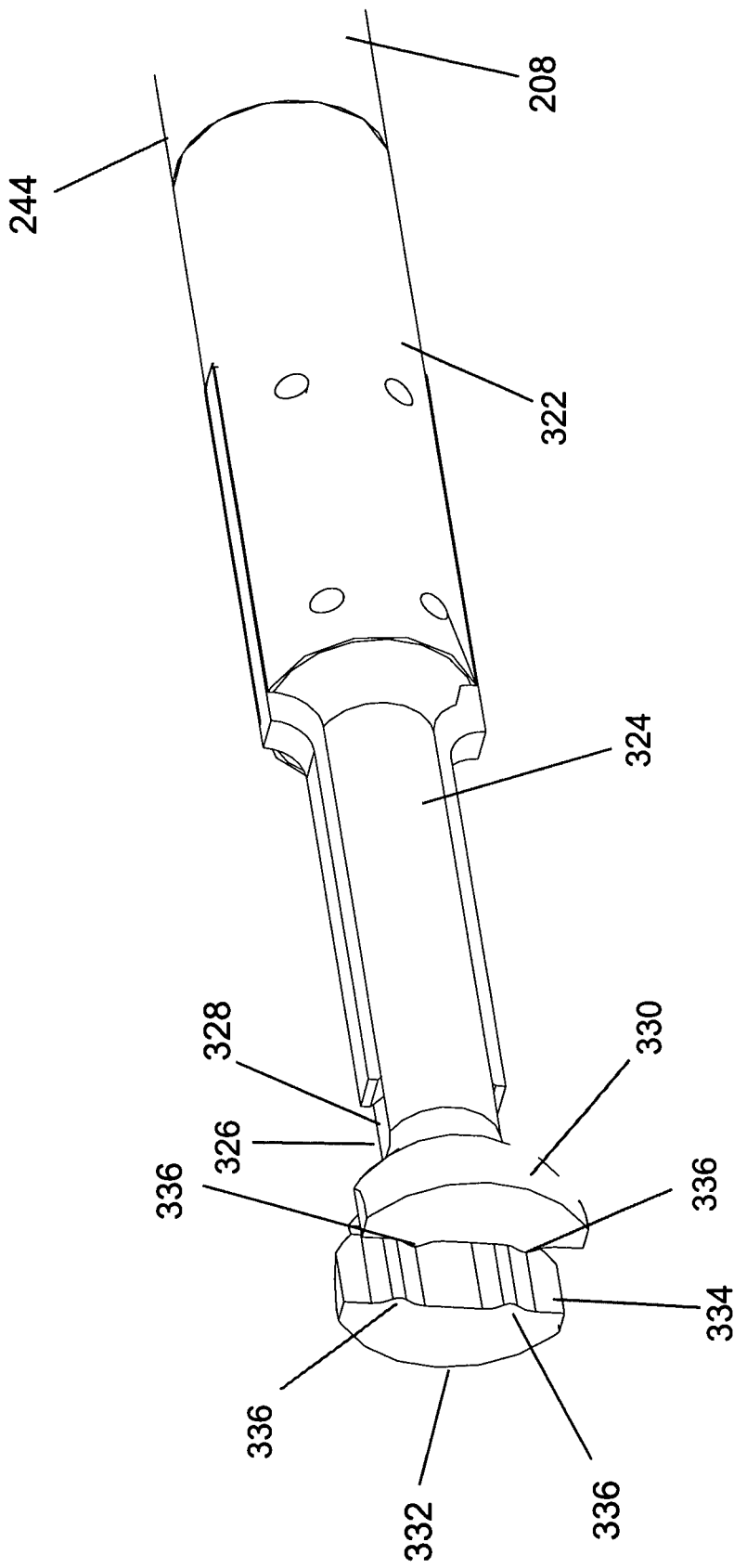
FIG. 28 depicts an isometric view of the crimping mechanism collett of the medical device of FIG. 27.

Referring to FIGS. 27 and 28, medical device 320 includes collett 322. As with collett 242, previously disclosed and illustrated, collett 322 is affixed to the second end portion 244 of the collett holder 208, opposite the cable tensioner 216. The collett 322 defines a collett passage longitudinally aligned with the longitudinal passage of the collett holder 208, along the central longitudinal axis A. An end portion of the collett 322 is bisected, forming first and second collett arms 324 and 326. A gap portion 328 is provided between the first and second collett arm 324 and 326. Each of the first and second collett arms 324 and 326 includes force application end portions 330 and 332. The force application end portions 330 and 332 combine to form a fastener aperture 334 configured to receive the fastener therein. The force application end portions 330 and 332 each include opposing compressive members 336 for compressing the fastener about the suture.

Figure 29:
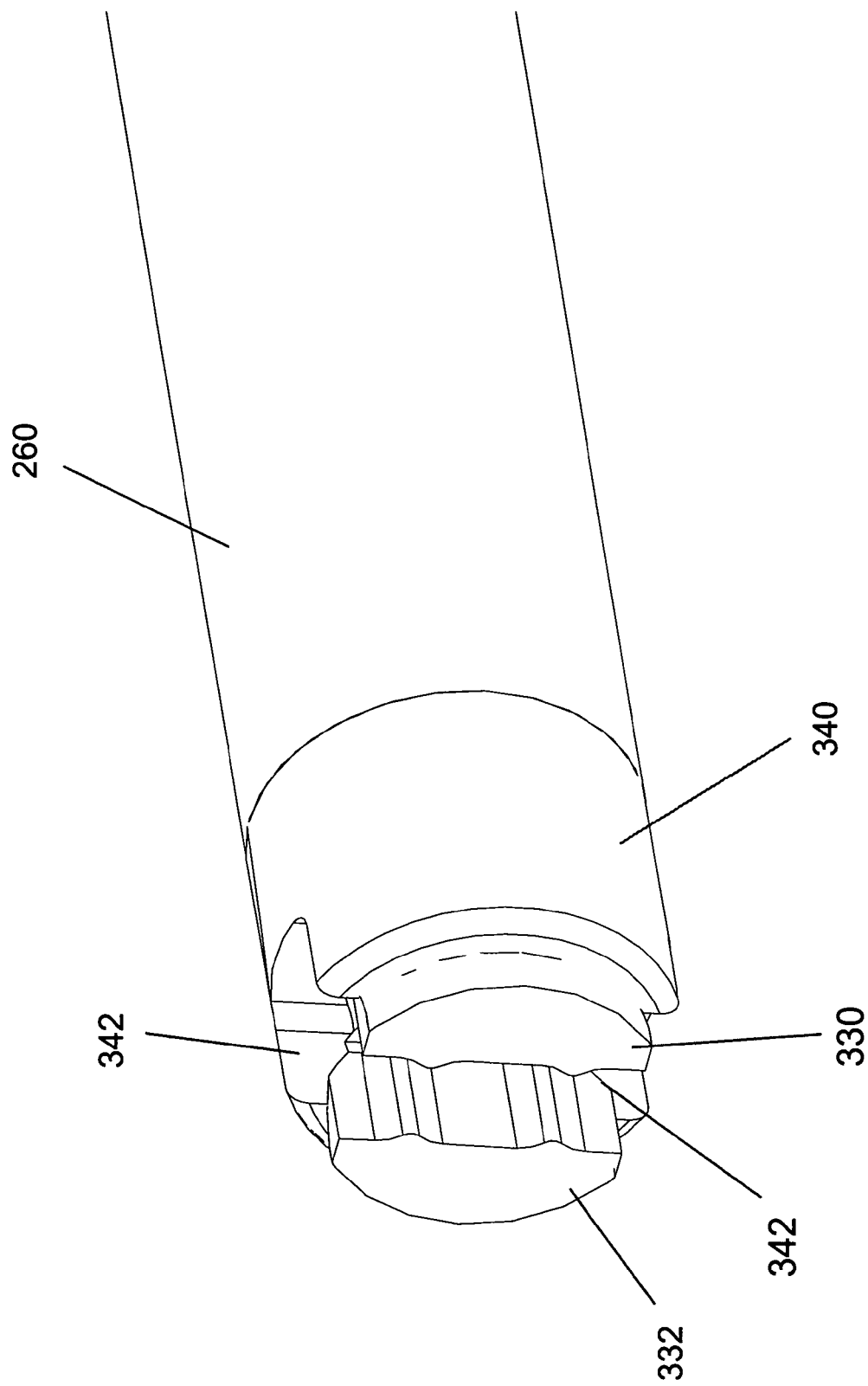
FIG. 29 depicts an isometric view of the crimping mechanism collett closer of the medical device of FIG. 27.

Referring to FIG. 27 and 29, medical device 320 includes collett closer 340. The collett closer 340 is positioned on the outer tube 260 proximal to the force application end portions 330 and 332 of the first and second collett arms 324 and 326. The collett closer 340 includes slotted sections 342 configured for receiving end portions of the fastener therein. As the outer tube 260 is moved from the first tube position P1 to the second tube position P2, the collett closer is moved over the force application end portions 330 and 332. Similar to collett closer 268, the collett closer 340 includes inner tapered surfaces 280 (See FIG. 22), such that the inner tapered surfaces 280 apply compressive forces to the force application end portions 330 and 332 as the collett closer 340 is moved over the force application end portions 330 and 332, closing the gap 328 there between.

Figure 30:
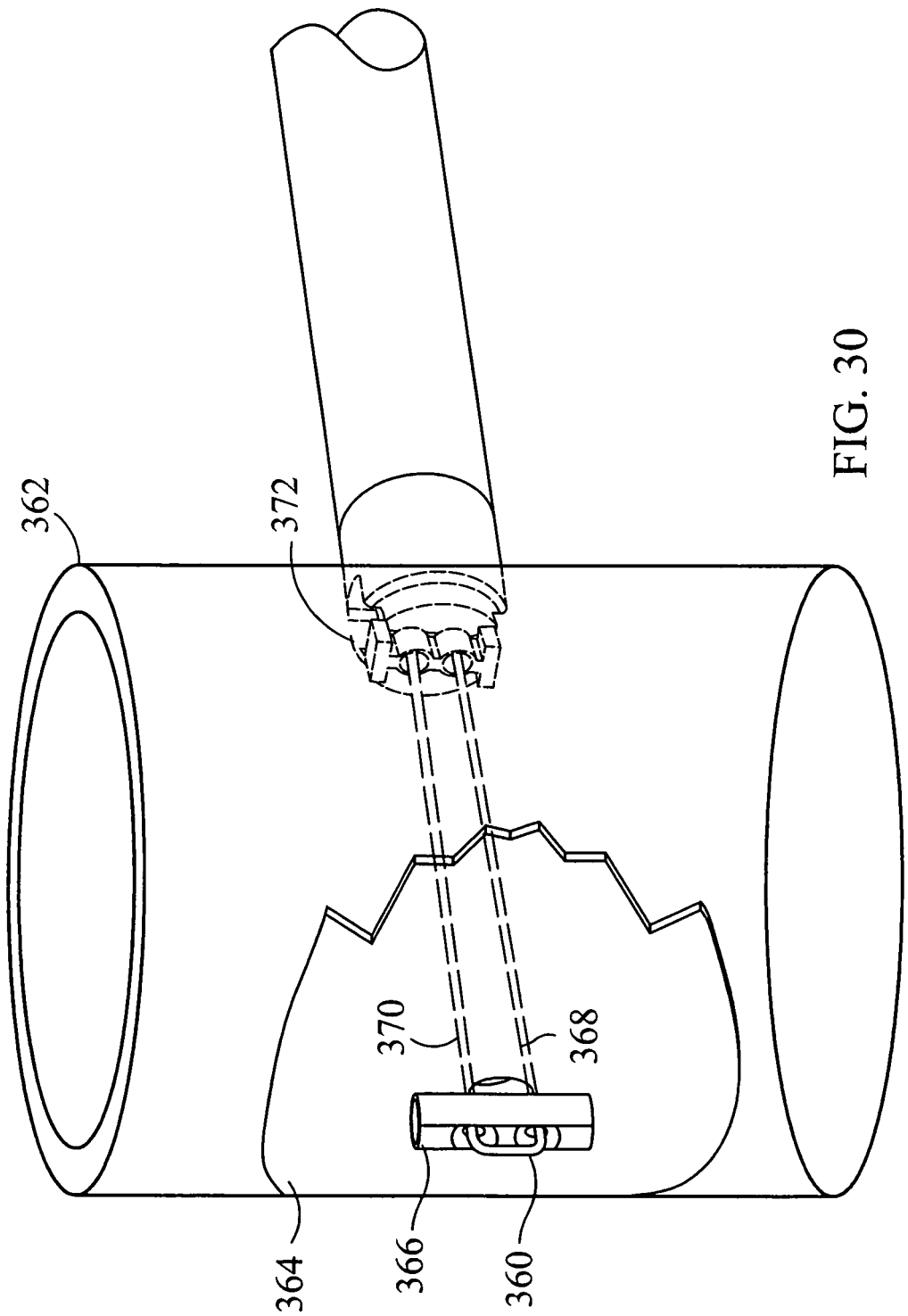
FIG. 30 depicts a sectional view of the medical device of FIG. 27 in use to secure a bone fracture.
Figure 31:
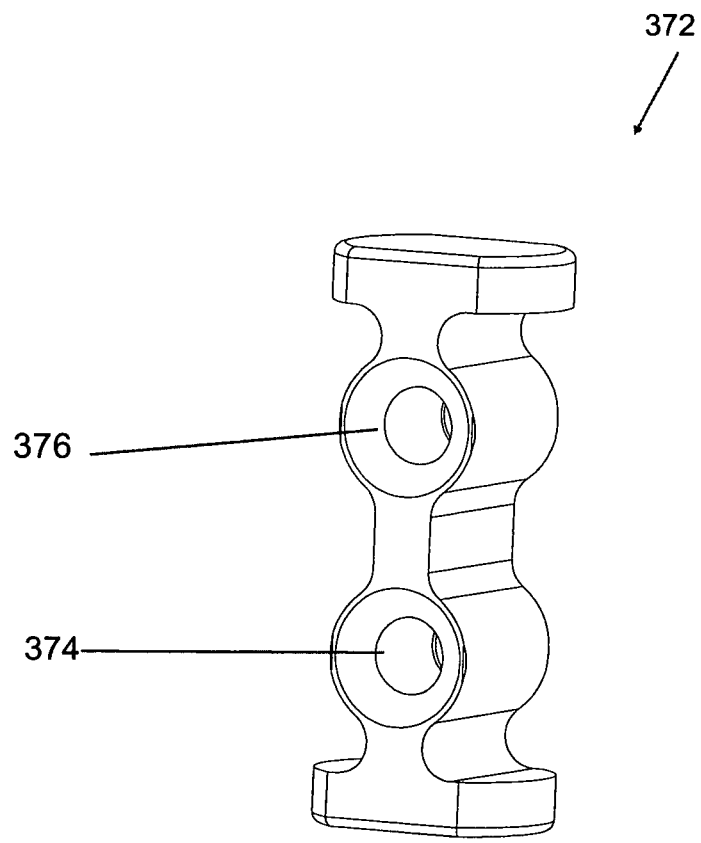
FIG. 31 depicts an exemplary fastener for use with the medical device of FIG. 27.

Referring to FIGS. 30 and 31, in a method of use suture 360 is inserted through the bone 362 and fracture 364, where the suture 360 is threaded through a fastener 366 on a first side (fracture side) of the bone 362. The suture 360 is reinserted through the fracture 364 and bone 362, such that first and second ends 368 and 370 of the suture 360 extend from the bone 362. The first and second ends of the suture 368 and 370 are threaded through a fastener 372, where the first end of the suture 368 is threaded through a first aperture 374 in the fastener 372 and the second end of the suture 370 is threaded through a second aperture 376 in the fastener 372.

Referring also to FIG. 26, the ends of the suture 368 and 370 are inserted through the medical device 320 along the central longitudinal axis A, through the collett 322, collett holder 208, and the cable tensioner 216, positioning the fastener 372 in the fastener aperture 334 and extending the ends of the suture 368 and 370 through the cable aperture 224. To tension the suture 360, the cable tension lever 230 is actuated from the first lever position L1 to the second lever position L2, sliding the cable tensioner 216 along the collett holder 208 from the first tensioner position T1, into the handle portion 202 against the tension bias member 238, to the second tensioner position T2. The suture ends 368 and 370 are positioned through the radial groove 226 and wrapped about the circumferential groove 228 on the end portion 222 of the cable tensioner 216, securing the suture 360 to the cable tensioner 216. The cable tension lever 230 is released, such that tension bias member 238 biases the cable tensioner 216 from the second tensioner position T2 towards the first tensioner position T1. The movement of the cable tensioner 216 towards the first tensioner position T1 applies tension to the suture 360, compressing the fastener 372 against the bone 362. The applied tension can be selected by actuating the cable tension lever 230 to the desired tension marking 240.

The trigger 264 is actuation from the first trigger position TR1 to the second trigger position TR2. The actuation of the trigger 264 slides the outer tube 260 along the collett holder 208 from the first tube position P1 to the second tube position P2, moving collett closer 340 about the force application end portions 330 and 332 of the first and second collett arms 324 and 326. The inner tapered surfaces 280 of the collett closer 340 apply compressive forces to the first and second force application end portions 330 and 332, compressing compressive members 336 of the first and second force application end portions 330 and 332 into the first and second fastener apertures 374 and 376. The compressive forces crimp the first and second fastener apertures 374 and 376 about the suture ends 368 and 370, securing the fastener 372 to the suture ends 368 and 370.

Simultaneously, the actuation of the trigger 264 results in the top portion 290 of the trigger 264 engaging the cut off cam ring 288, sliding the cut off cam ring 288 and cut off cam 284 along the collett holder 208. The second end portion 200 of the cut off cam 283 engages the angular surface 298 of the cutting head 294, forcing the cutting edge 296 into the suture ends 268 and 270, cutting the suture ends 368 and 370.

Figure 32:
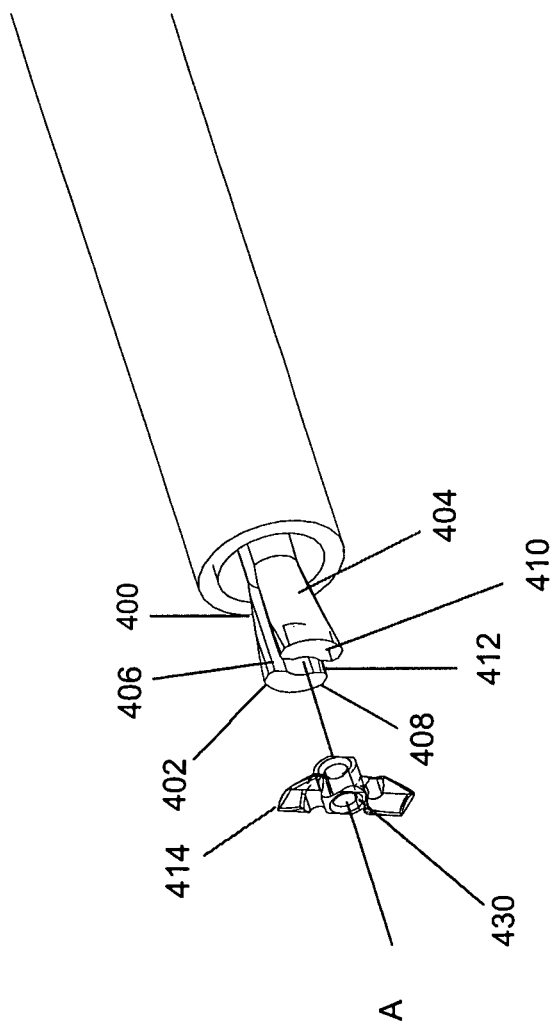
FIG. 32 depicts an alternative sectional view of the medical device of FIG. 27 in use to secure a bone fracture.

Referring to FIG. 32, similar to FIGS. 18 and 20, a collett 400 is affixed to a second end portion 244 of the collett holder 208, opposite the cable tensioner 216. The collett 400 defines a collett passage longitudinally aligned with the longitudinal passage of the collett holder 208 along the central longitudinal axis A. An end portion of the collett 400 is bisected, forming first and second collett arms 402 and 404. A gap portion 406 is provided between the first and second collett arms 402 and 404. Each of the first and second collett arms 402 and 404 includes force application end portions 408 and 410. The force application end portions 408 and 410 combine to form a bushing aperture 412 configured to received the bushing therein 414. The collett 400 is made of a semi-rigid material, such that the first and second collett arms 402 and 404 can be moved from an open to a closed position, closing the gap 406 between the force application end portions 408 and 410.

Figure 33:
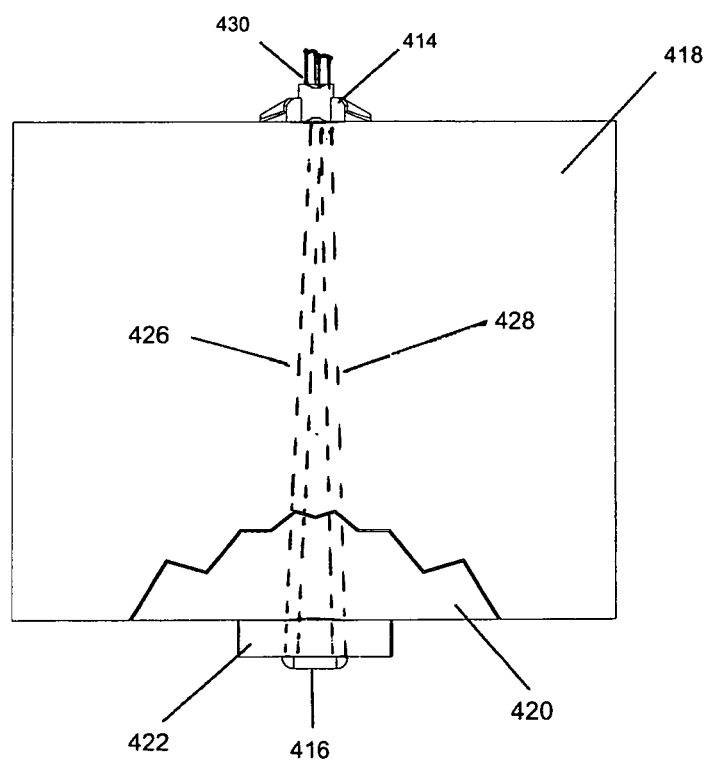
FIG. 33 depicts an alternative fastener for use with the medical device of FIG. 32.

Referring also to FIG. 33, in a method of use, suture 416 is inserted through the bone 418 and fracture 420, where the suture 416 is threaded through a fastener 422 on a first side (fracture side) of the bone 424. The suture 416 is reinserted through the fracture 420 and bone 418, such that first and second ends 426 and 428 of the suture 416 extend from the bone 418. The first and second ends of the suture 426 and 428 are threaded through a fastener 414, where the first and second ends 426 and 428 of the suture 416 is threaded through an aperture 430 in the fastener 414.

Referring also to FIGS. 26 and 29, the ends of the suture 426 and 428 are inserted through the medical device 320 along the central longitudinal axis A, through the collett 400, collett holder 208, and the cable tensioner 216, positioning the fastener 414 in the fastener aperture 412 and extending the ends of the suture 426 and 428 through the cable aperture 224. To tension the suture 416, the cable tension lever 230 is actuated from the first lever position L1 to the second lever position L2, sliding the cable tensioner 216 along the collett holder 208 from the first tensioner position T1, into the handle portion 202 against the tension bias member 238, to the second tensioner position T2. The suture ends 426 and 428 are positioned through the radial groove 226 and wrapped about the circumferential groove 228 on the end portion 222 of the cable tensioner 216, securing the suture 360 to the cable tensioner 216. The cable tension lever 230 is released, such that tension bias member 238 biases the cable tensioner 216 from the second tensioner position T2 towards the first tensioner position T1. The movement of the cable tensioner 216 towards the first tensioner position T1 applies tension to the suture 416, compressing the fastener 414 against the bone 418. The applied tension can be selected by actuating the cable tension lever 230 to the desired tension marking 240.

The trigger 264 is actuated from the first trigger position TR1 to the second trigger position TR2. The actuation of the trigger 264 slides the outer tube 260 along the collett holder 208 from the first tube position P1 to the second tube position P2, moving collett closer 340 about the force application end portions 408 and 410 of the first and second collett arms 402 and 404. The inner tapered surfaces 280 of the collett closer 340 apply compressive forces to the first and second force application end portions 408 and 410. The compressive forces crimp the aperture 430 about the suture ends 426 and 428, securing the fastener 414 to the suture ends 426 and 428.

Figure 36:
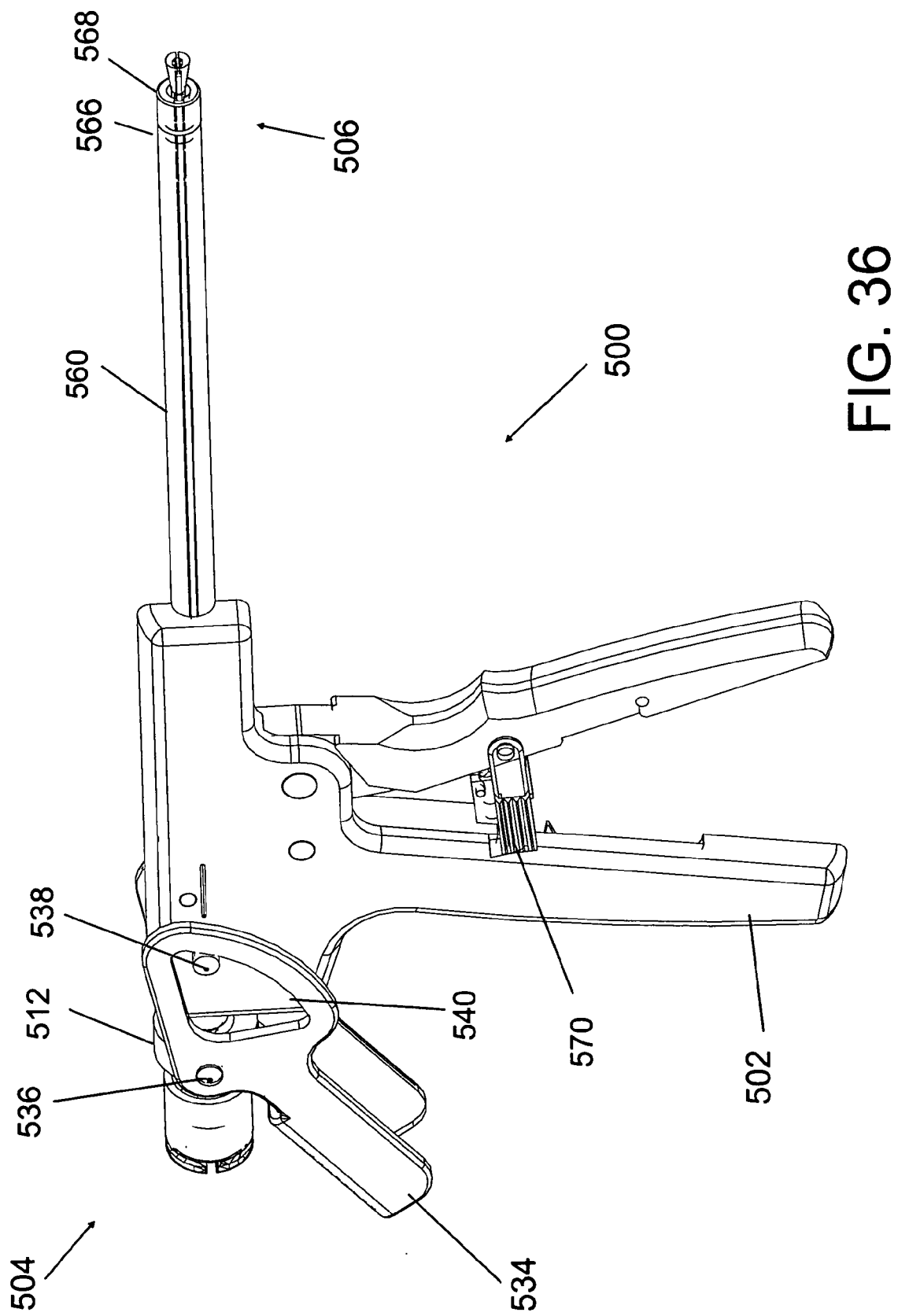
FIG. 36 depicts a front isometric view of the medical device of the present invention.

Referring to FIG. 36, a medical device 500 is provided for securing the bushing to the cable. The medical device 500 includes a handle portion 502 having a tensioning mechanism 504, tensioning the cable and applying a force to the bushing, and a crimping mechanism 506 for securing the bushing to the cable.

Figure 37:
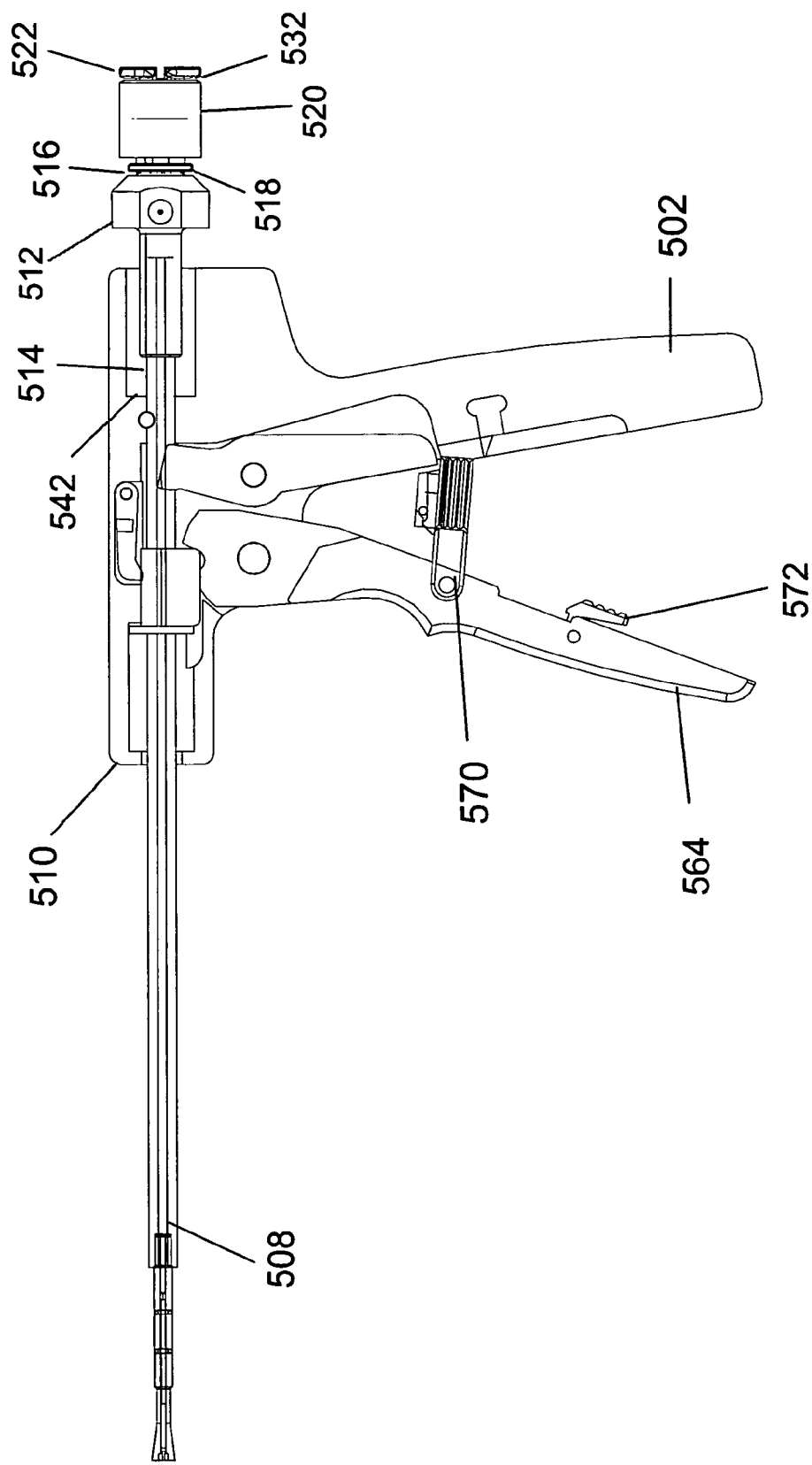
FIG. 37 depicts a side sectional view showing the tensioning mechanism of the medical device of FIG. 36.
Figure 38:
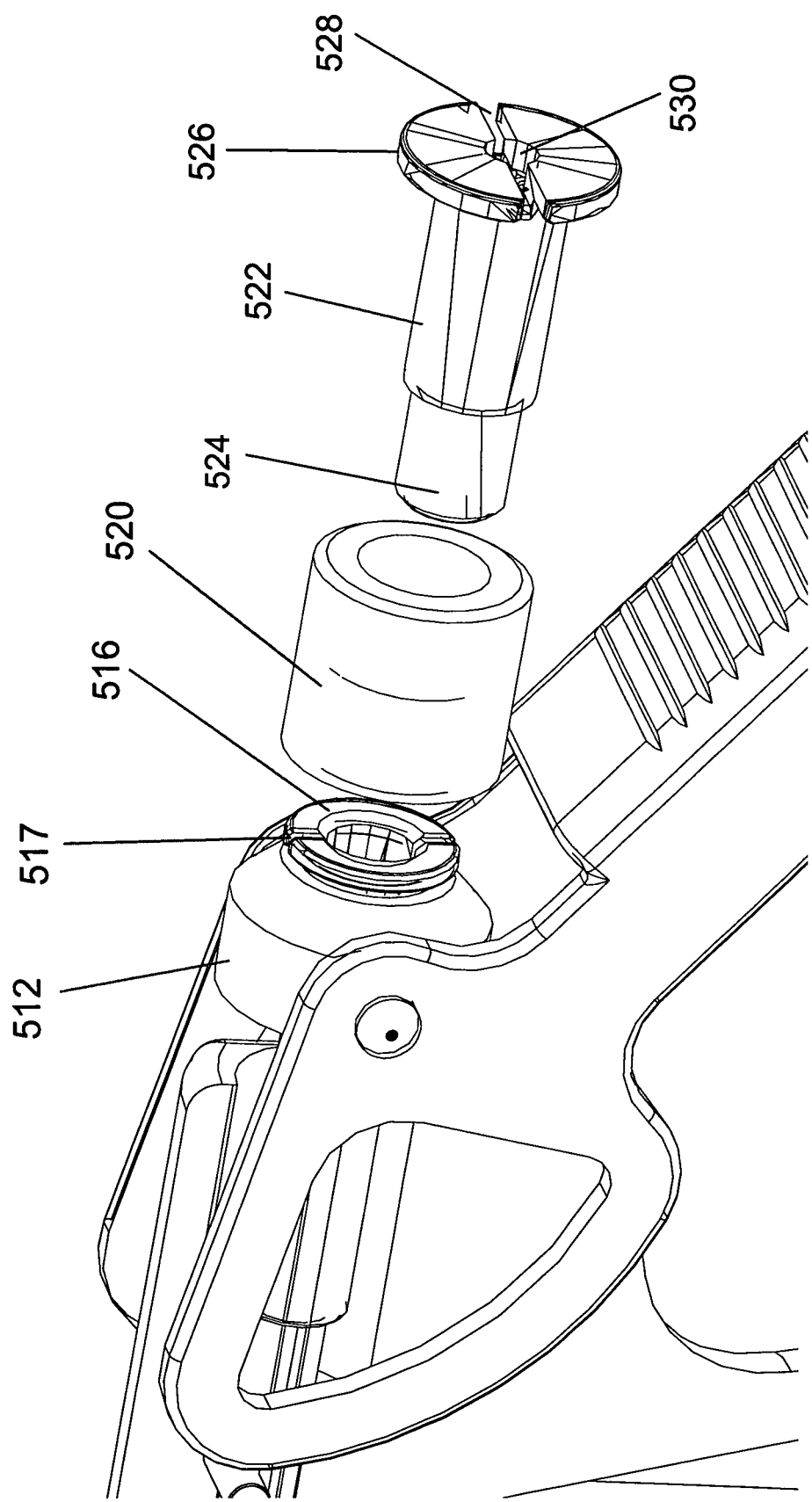
FIG. 38 depicts a rear exploded view showing the tensioning mechanism of the medical device of FIG. 36.

Referring also to FIGS. 37 and 38, the tensioning mechanism 504 includes a collett holder 508 defining a longitudinal passage along a central longitudinal axis A. The collett holder 508 is affixedly positioned through a top portion 510 of the handle portion 502. A cable tensioner 512 is slidably positioned on a first end 514 of the collett holder 508. The cable tensioner 512 defines a cable passage longitudinally aligned with the longitudinal passage of the collett holder 508. An end portion 516 of the cable tensioner 512 includes a cable aperture for threading the cable there through. A radial groove and circumferential groove 518 are provided on the end portion 516 of the cable tensioner 512, such that the cable can be wrapped about the circumferential groove 518 of the cable tensioner 512, thereby preventing relative movement between the cable and the cable tensioner 512.

In an exemplary embodiment, the cable tensioner 512 can include a retention bushing 520 and a tension insert 522. The tension insert 522 defines a cable passage longitudinally aligned with the longitudinal passage of the cable tensioner 512. The retention bushing 520 is positioned about a portion of the tension insert 522, where an end portion 524 is threaded into the end portion 516 of the cable tensioner 512. An opposite end portion 526 of the tension insert 522 includes a cable aperture 528 for threading the cable there through. A radial groove 530 is provided on the end portion 526 of the cable tensioner 512 and the retention bushing 520 and the tension insert 522 combine to form a circumferential groove 532, such that the cable can be wrapped about the circumferential groove 532, thereby preventing relative movement between the cable and the cable tensioner 512.

A cable tension lever 534 is pivotally connected to the cable tensioner 512 with a lever pin 536. The cable tension lever 534 is adjustably positioned on the handle portion 502 with body pins 538, wherein a body pin 538 is mirrorly positioned on opposite sides of the handle portion 502. The body pins 538 are engaged in the cable tension lever 536 arcuate lever slots 540, such that cable tension lever 534 and cable tensioner 512 are movably connected to the handle portion 502.

In use, as the cable tension lever 534 is pivoted about the cable tensioner 512 from a first lever position L1 to a second lever position L2, the body pins 538 traverse the arcuate lever slots 540, resulting in a translation of the cable tensioner 512 along the first end 514 of the collett holder 508 from a first tensioner position T1 to a second tensioner position T2. A tension bias member 542 is interposed between the cable tensioner 512 and the handle portion 502, biasing the cable tensioner 512 into the first tensioner position T1.

Figure 39:
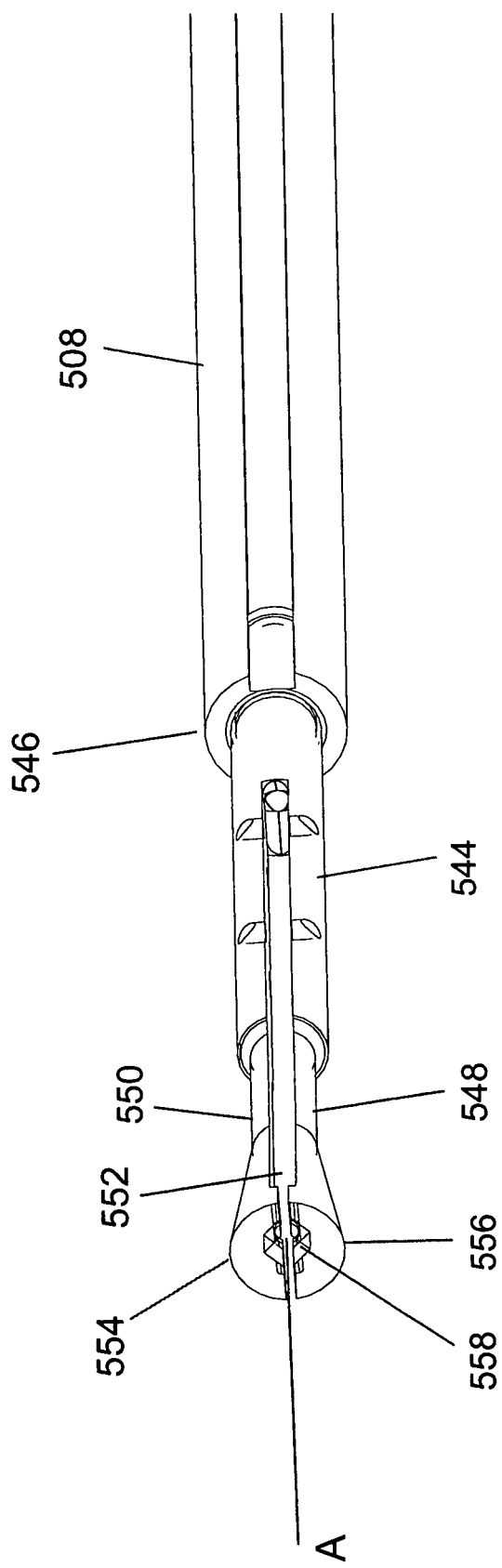
FIG. 39 depicts an isometric view of the crimping mechanism collett of the medical device of FIG. 36.

Referring to FIGS. 37 and 39, a collett 544 is affixed to a second end portion 546 of the collett holder 508, opposite the cable tensioner 512. The collett 544 defines a collett passage longitudinally aligned with the longitudinal passage of the collett holder 508 along the central longitudinal axis A. An end portion of the collett 544 is bisected, forming first and second collett arms 548 and 550. A gap portion 552 is provided between the first and second collett arms 548 and 550. Each of the first and second collett arms 548 and 550 includes force application end portions 554 and 556. The force application end portions 554 and 556 combine to form a bushing aperture 558 configured to received the bushing therein. The collett 544 is made of a semi-rigid material, such that the first and second collett arms 548 and 550 can be moved from an open to a closed position, closing the gap 552 between the force application end portions 554 and 556.

In use, the tensioning mechanism 504 is used to tension the cable. The cable can include single or multiple filaments. The cable is inserted through the medical device 500 along the central longitudinal axis A, through the collett 544, collett holder 508, and the cable tensioner 512, positioning the bushing in the bushing aperture 558 and extending the cable through the cable aperture 530. To tension the cable, the cable tension lever 354 is actuated from the first lever position L1 to the second lever position L2, sliding the cable tensioner 512 along the collett holder 508 from the first tensioner position T1, into the handle portion 502 against the tension bias member 542, to the second tensioner position T2. The cable is positioned through the radial groove 528 and wrapped about the circumferential groove 532 on the between the retention bushing 520 and the tension insert 522, securing the cable to the cable tensioner 512. The cable tension lever 534 is released, such that tension bias member 542 biases the cable tensioner 512 from the second tensioner position T2 towards the first tensioner position T1. The movement of the cable tensioner 512 towards the first tensioner position T1 applies a tension to the cable, forcing the bushing into the second fastener. The applied tension can be selected by actuating the cable tension lever 534 to the desired tension.

Figure 40:
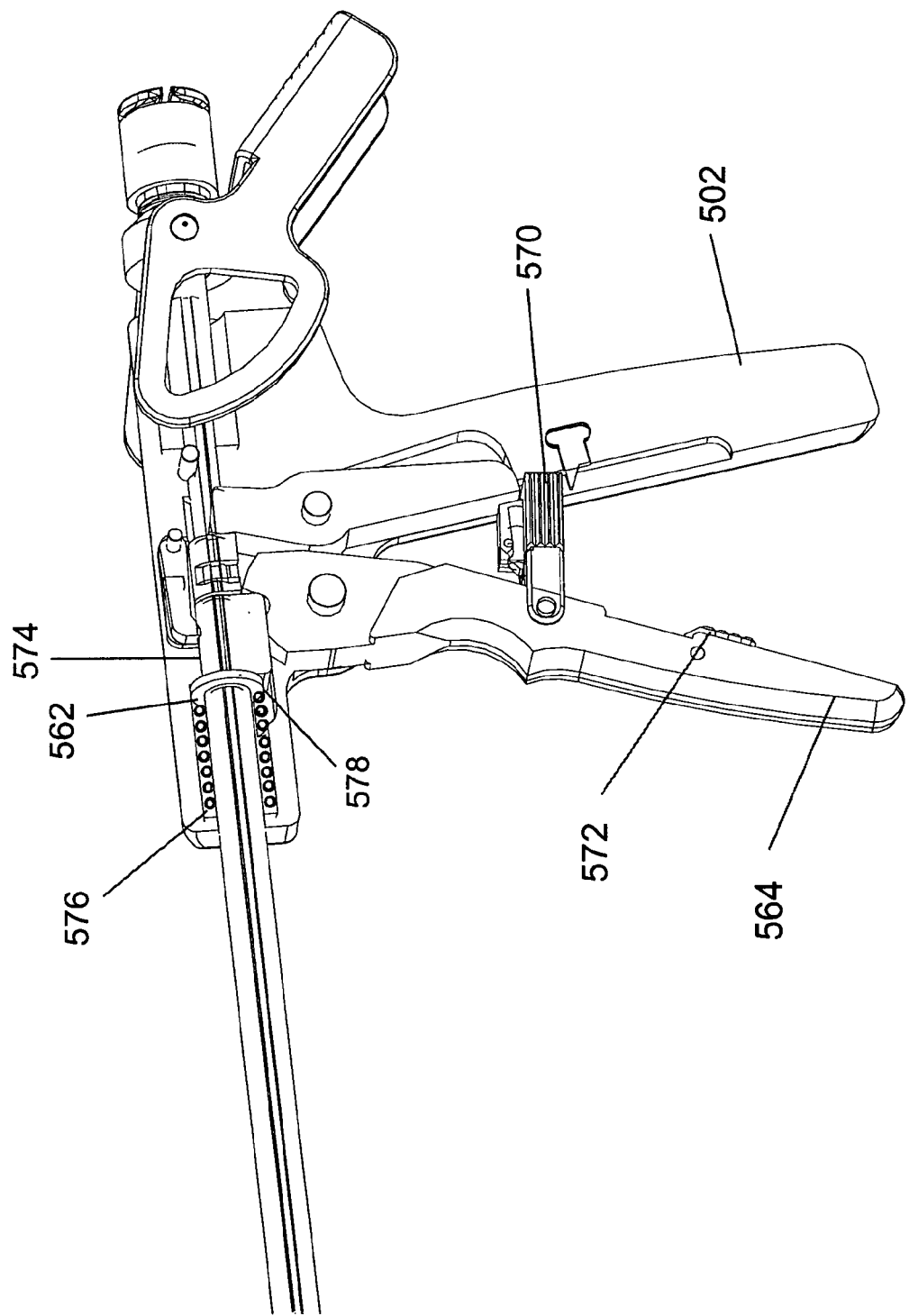
FIG. 40 depicts a partial isometric view showing the handle portion of the crimping mechanism of the medical device of FIG. 36.

Referring to FIGS. 36 and 40, the crimping mechanism 506 includes an outer tube 560 slidingly positioned over the collett holder 508. The outer tube 560 includes a first end 562 operably connected to a trigger 564 and a second end 566 connected to a collett closer 568. The trigger 264 is pivotally mounted in the handle portion 502, such that the trigger 564 can be actuated from a first trigger position TR1 to a second trigger position TR2. A locking mechanism 570 prevents the trigger 564 from being actuated. The locking mechanism 570 is disengaged by rotating it away from the handle, where the locking mechanism is secured to the trigger with the locking pawl 572. (See also FIG. 37).

The operable connection between the first end of the outer tube 562 and the trigger 564 includes an outer tube ferrule 574 slidably positioned about the collett holder 408 and affixed to the first end of the outer tube 562. A tube bias member 576 is interposed between the handle portion 502 and the outer tube ferrule 574, such that the tube bias member 576 biases the outer tube ferrule 574 and the outer tube 560 into a first tube position P1. A tube washer 578 can be provided between the tube ferrule 574 and the bias member 576.

An actuation of the trigger 564 from a first trigger position TR1 to a second trigger position TR2 translates the outer tube ferrule 574 along the collett holder 208 from the first tube position P1 to a second tube position P2. In the second tube position P2 a tube pawl 580 engages the outer tube ferrule 574, hold the outer tube ferrule in the second tub position P2.

Figure 42:
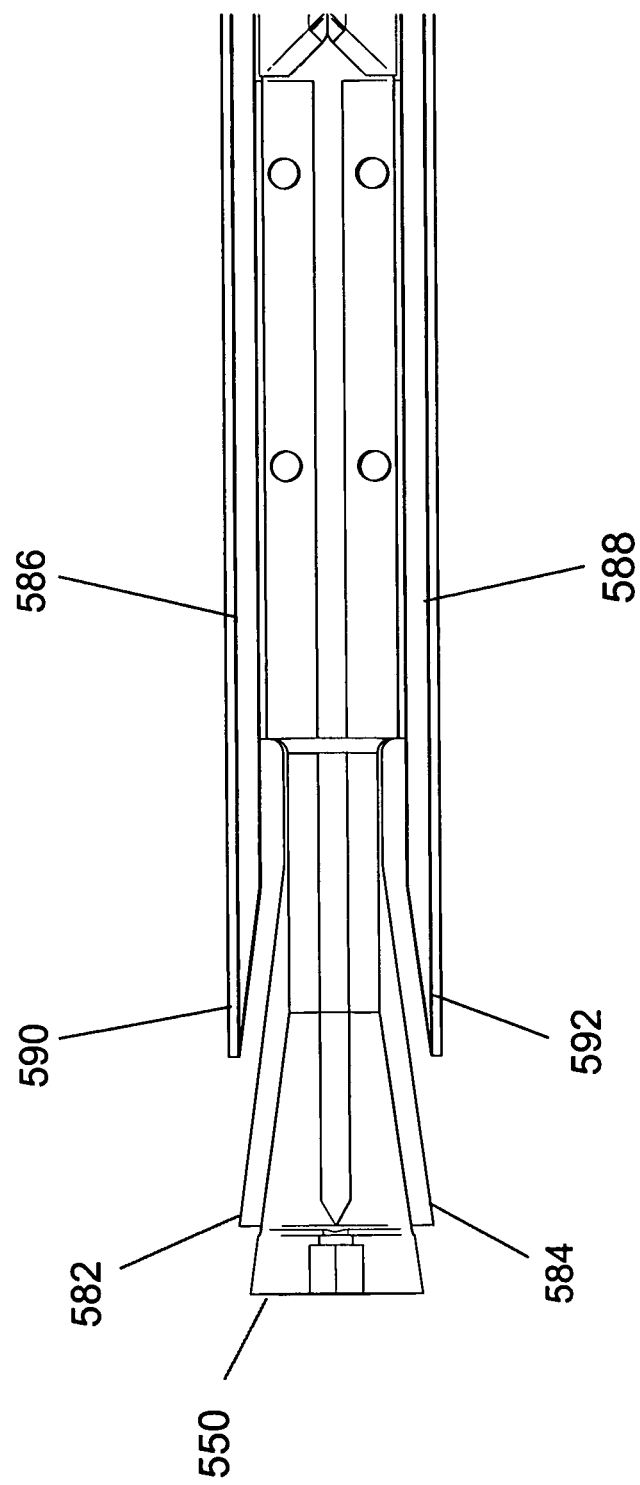
FIG. 42 depicts an isometric view of the cutting mechanism in the collett of the medical device of FIG. 36.

Referring to FIGS. 36 and 42, the collett closer 568 is positioned on the outer tube 560 proximal to the force application end portions 554 and 556 of the first and second collett arms 548 and 550. As the outer tube 560 is moved from the first tube position P1 to the second tube position P2, the collett closer 568 is moved over the force application end portions 554 and 556. The collett closer 568 includes inner tapered surfaces 582, such that the inner tapered surfaces 580 apply compressive forces to the force application end portions 554 and 556 as the collett closer 568 is moved over the force application end portions 554 and 556, closing the gap 552 there between.

In use, the trigger 564 is actuated from the first trigger position TR1 to the second trigger position TR2. The actuation of the trigger 564 slides the outer tube 560 along the collett holder 508 from the first tube position P1 to the second tube position P2, moving collett closer 568 about the force application end portions 554 and 556 of the first and second collett arms 548 and 550. The inner tapered surfaces 580 of the collett closer 568 apply compressive forces to the first and second force application end portions 554 and 556, closing the gap 552 there between.

Figure 41:
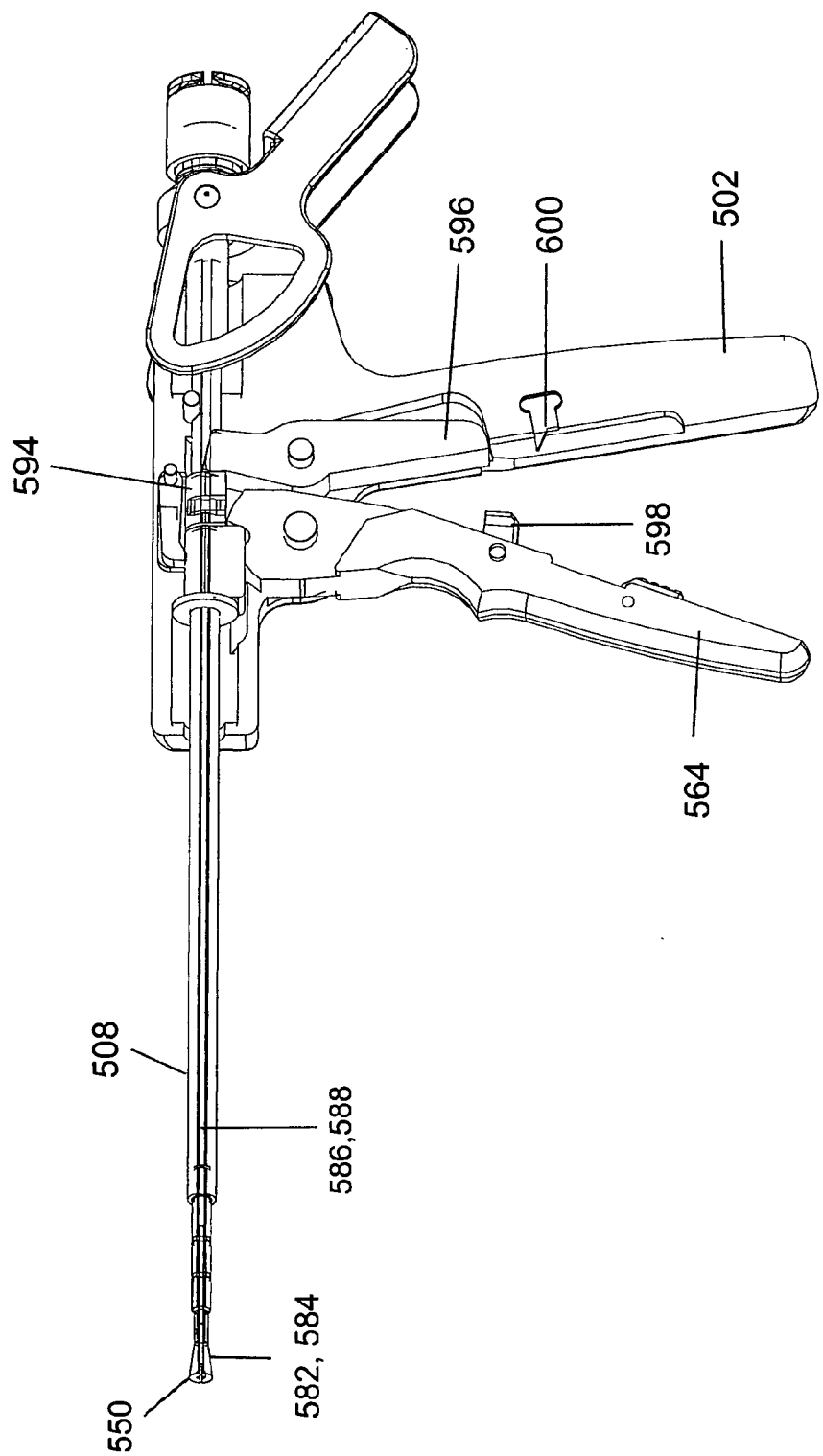
FIG. 41 depicts a partial isometric view showing the cutting mechanism of the medical device of FIG. 36.
Figure 43:
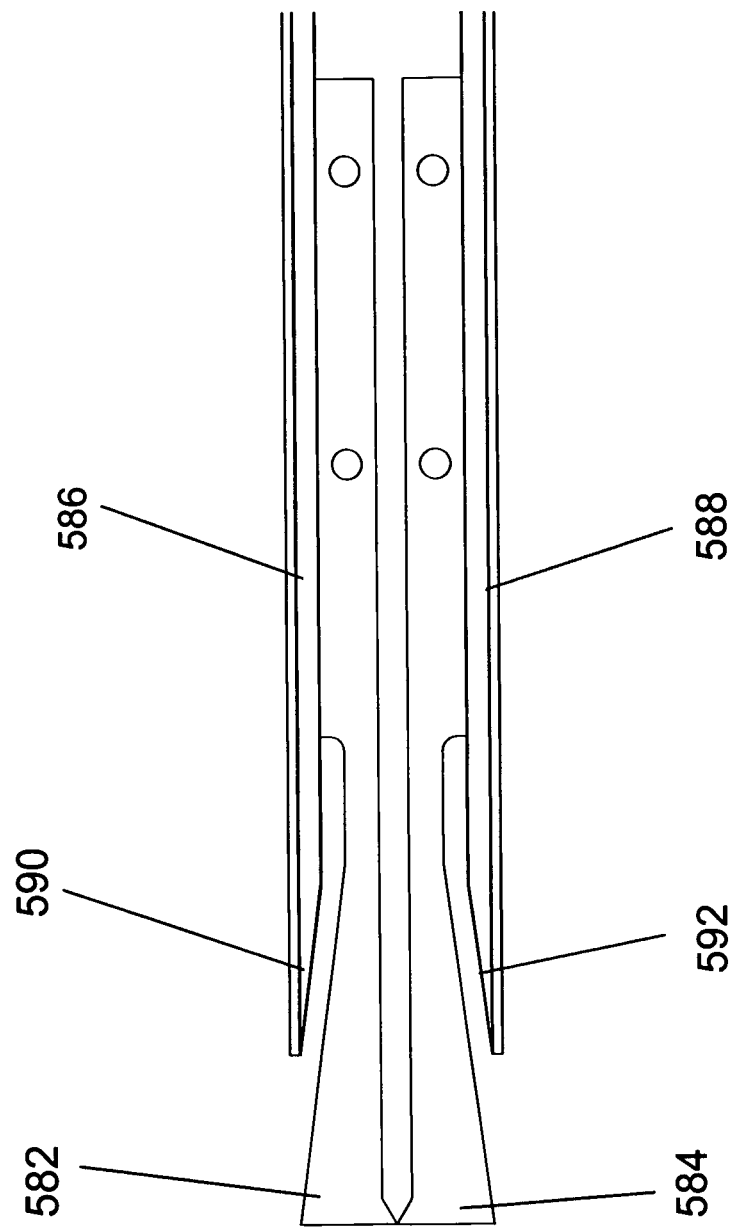
FIG. 43 depicts the cutting wedge of the medical device of FIG. 36.

Referring to FIGS. 41-43, the crimping mechanism 506 can further include a cutting mechanism. The cutting mechanism includes a pair of cut off cams 582 and 584 positioned in the collett gap 552. A pair of wedges 586 and 588 are slidingly positioned along and on opposite sides of the collett 550 and the collett holder 508. Each of the wedges 586 and 588 include tapered ends 590 and 592 positioned proximal to the cut off arms, such that when the wedges are moved from a first wedge position W1 to a second wedge position W2, the tapered ends 590 and 592 compress the cut off cams 582 and 584 together, cutting the cable.

The handle 502 further includes a wedge pusher 594 slidingly positioned about the collett holder 508, adjacent to second ends 594 and 596 of wedges 586 and 588. The wedge pusher 594 is slidable from a first position to a second position, such that the wedges 586 and 588 are moved from the first wedge position W1 to the second wedge position W2. A rocker 596 is pivotally connected to the handle 502, such that an actuation of the rocker 596 from a first rocker position R1 to a second rocker position R2, slides the wedge pusher 594 from the first position to the second position, moving wedges 586 and 588 from the first wedge position W1 to the second wedge position W2

Figure 44:
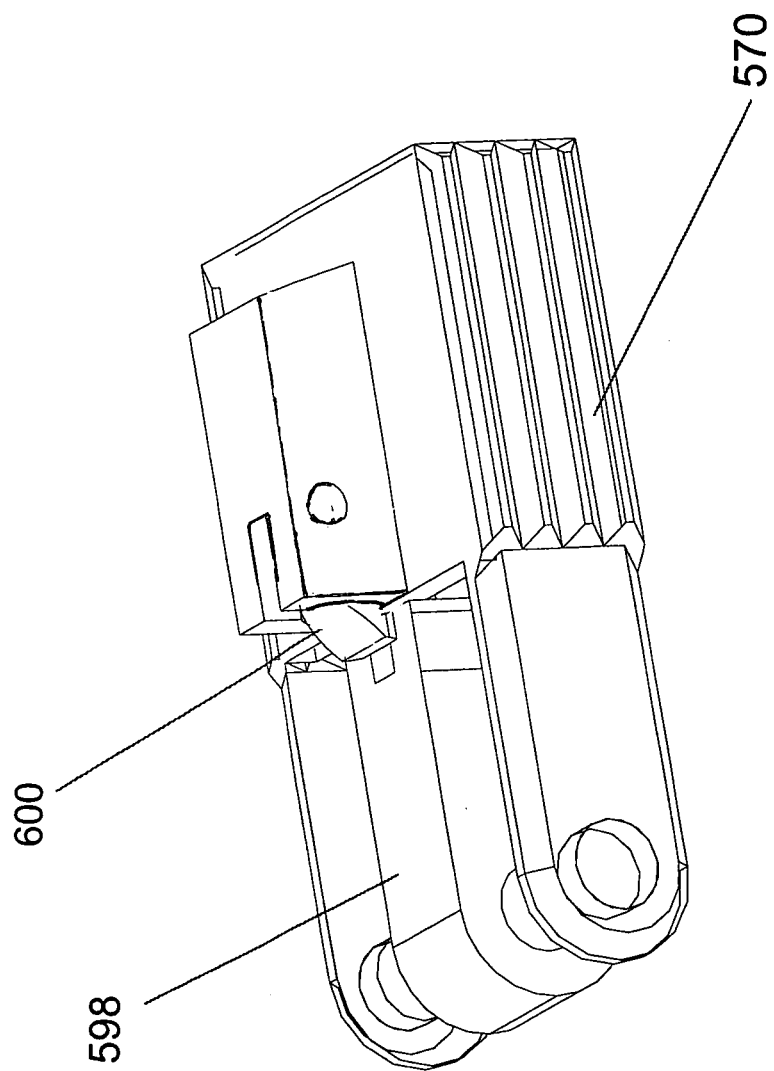
FIG. 44 depicts a safety lock of the medical device of FIG. 36.

Referring to FIGS. 41 and 44, the locking mechanism 570 includes a rocker kicker 598 pivotally affixed therein. The rocker kicker 598 is biasedly connected to the locking mechanism 570, being held in a closed position by a pin 600. When the trigger 564 is actuated from the first trigger position TR1 to the second trigger position TR2, the release 602 engages the pin 600, releasing the rocker kicker 590.

The trigger 564 is released, allowing the trigger 564 to move from the second trigger position TR2 to the first trigger position TR1. To actuate the cutting mechanism, the trigger is again moved from the first trigger position TR1 to the second trigger position TR2, such that the rocker kicker 598 engages the rocker 596, pivoting the rocker 596 from the first rocker position R1 to the second rocker position. The rocker 596 slides the wedge pusher 594 from the first position to the second position, moving wedges 586 and 588 from the first wedge position W1 to the second wedge position W2, such that, the tapered ends 590 and 592 compress the cut off cams 582 and 584 together, cutting the cable. The trigger 564 can then be released, releasing the crimped fastener.

It is also contemplated that the system and medical device of the present invention may be disposable or may be sterilized after use and reused.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include biodegradable plates, porcine or bovine patches, metallic fasteners, compliant bearings for one or more compartments of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled Apparatus and Method for Use in Positioning a Suture Anchor, discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

In addition, intramedullary fracture fixation and comminuted fracture fixation may be achieved with the devices and methods of the present invention. For example, a plate or rod may be positioned within or against the fractured bone. A fastener may be driven through or about the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention. Therefore, it will be understood that the appended claims are intended to cover all such modifications and embodiments which come within the spirit and scope of the present invention.

What is claimed is:

1. A tissue fixation system comprising:
an elongate flexible member; and
a fastener configured for implantation in the body, the fastener configured to be positionable on the flexible member and movable from a first orientation to a second orientation without disconnecting from the flexible member, the fastener having a body with a first surface and a tapered portion defined by a leading end surface and the first surface and a second surface parallel to the first surface and defined between the leading end surface and a trailing end surface, the first surface including a substantially flat portion configured to be positionable against a tissue section, and the fastener body including a bore extending from the first surface to the second surface and configured to receive a portion of the flexible member at an angle with respect to the flat portion,
wherein said flat portion is positionable against the tissue section in the second orientation by tensioning the flexible member.

2. The tissue fixation system of claim 1 wherein the second surface includes a channel configured to receive a portion of the flexible member in the first orientation.

3. The tissue fixation system of claim 1 wherein the fastener body includes a groove configured to receive a portion of the flexible member to reduce a profile of the fastener in at least the first or second orientation.

4. The tissue fixation system of claim 3 wherein the groove extends toward the leading end surface.

5. The tissue fixation system of claim 3 further comprising a biasing means for maintaining the fastener in the first orientation.

6. The tissue fixation system of claim 5 wherein the biasing means comprises an adhesive between a groove on the first surface and the portion of the flexible member received in the groove.

7. The tissue fixation system of claim 5 wherein the biasing means comprises a frangible connection between a groove on the first surface and the portion of the flexible member received in the groove.

8. The tissue fixation system of claim 1 wherein the fastener includes a taper.

9. The tissue fixation system of claim 1 wherein the second surface of the fastener body includes a well surrounding the bore.

10. The tissue fixation system of claim 1 wherein a distal end of the flexible member includes a stop larger than the bore.

11. The tissue fixation system of claim 10 wherein the well is configured and dimensioned to receive at least a portion of the stop.

12. The tissue fixation system as set forth in claim 1 further comprising a second fastener that includes a first surface having a substantially flat portion configured to be positionable adjacent the second tissue section and a bore extending from the first surface through a second surface.

13. The tissue fixation system of claim 1 wherein the fastener is pivotable from the first orientation to the second orientation and the first surface is configured to contact a tissue section in the second orientation.

14. The tissue fixation system of claim 1 wherein the first and second surfaces are substantially parallel.

15. The tissue fixation system of claim 1 wherein the bore is substantially perpendicular to the first or second surface.

16. The tissue fixation system of claim 1 wherein the fastener includes at least a deformable portion.

17. The tissue fixation system of claim 1 wherein the fastener includes at least a rounded portion.

18. The tissue fixation system of claim 1 wherein the leading or trailing end surface of the fastener is narrower than a majority of the fastener body.

19. A tissue fixation system to secure a first tissue section relative to a second tissue section, comprising:
   an flexible member positionable in at least a portion of the first and second tissue sections;
   a first fastener configured for implantation in the body, the first fastener configured to be movable from a first orientation to a second orientation and positionable on the flexible member, the first fastener having a body with a first surface and a tapered portion defined by a leading end surface and the first surface and a second surface parallel to the first surface and defined between the leading end surface and a trailing end surface, the first surface including a substantially flat portion configured to be positionable adjacent the first tissue section, and the first fastener body including a bore extending from the first surface to the second surface and configured to receive a portion of the flexible member at an angle with respect to the flat portion, wherein a first end of the flexible member includes a stop larger than the bore; and
   a second fastener configured for implantation in the body, the second fastener configured to be positionable on the flexible member at a distance from the first fastener and adjacent to the second tissue section,
   wherein the flexible member is tensionable between the first and second fasteners.

20. The tissue fixation system of claim 19 wherein the first fastener is an anchor.

21. A tissue fixation system as set forth in claim 19 wherein the first fastener is moveable with respect to the flexible member from a first orientation to a second orientation without disconnecting from the flexible member.

22. The tissue fixation system as set forth in claim 21 further comprising a biasing means maintaining the first fastener in the first orientation.

23. The tissue fixation system as set forth in claim 22 wherein the biasing means comprises an adhesive between a groove on the first surface and the portion of the flexible member received in the groove.

24. The tissue fixation system as set forth in claim 22 wherein the biasing means comprises a frangible connection between a groove on the first surface and the portion of the flexible member received in the groove.

25. The tissue fixation system as set forth in claim 21 further comprising a bushing member positionable on the second end of the flexible member, adjacent to the second fastener, wherein the bushing member is affixable about the second end of the flexible member.

26. The tissue fixation system as set forth in claim 21 wherein the first fastener is pivoted from a first orientation to a second orientation in which the first surface contacts the first tissue section and the second fastener is pivoted from a first orientation to a second orientation and the first surface is configured to contact the second tissue section.

27. The tissue fixation system as set forth in claim 19 wherein the first fastener body includes a channel.

28. The tissue fixation system as set forth in claim 27 wherein the second surface of the first fastener body includes a well surrounding the bore.

29. The tissue fixation system as set forth in claim 28 wherein the first fastener is an anchor.

30. The tissue fixation system as set forth in claim 29 wherein the well is configured and dimensioned to receive at least a portion of the stop.

31. The tissue fixation system as set forth in claim 30 wherein the first fastener body includes a taper.

32. The tissue fixation system as set forth in claim 19 wherein the leading or trailing end surface includes an edge.

33. The tissue fixation system as set forth in claim 19 wherein the first surface includes a groove.

34. The tissue fixation system as set forth in claim 19 wherein the second fastener includes a first surface having a substantially flat portion configured to be positionable adjacent the second tissue section and a bore extending from the first surface through a second surface.

35. The tissue fixation system as set forth in claim 19 wherein the second fastener has a body with a first surface that includes a groove configured and dimensioned to receive a portion of the flexible member in a first orientation and a second surface opposite the first surface that includes a channel configured and dimensioned to receive a portion of the flexible member in the first orientation.

36. The tissue fixation system of claim 19 wherein the first and second surfaces are substantially parallel.

37. The tissue fixation system of claim 19 wherein the bore is substantially perpendicular to the first or second surface.

38. The tissue fixation system of claim 19 wherein the first or second fastener includes at least a deformable portion.

39. The tissue fixation system of claim 19 wherein the fastener includes at least a rounded portion.

40. The tissue fixation system of claim 19 wherein the leading or trailing end surface of the first fastener is narrower than a majority of the first fastener body.

41. A tissue fixation system comprising:
an elongate flexible member;
a fastener configured for implantation in the body, the fastener configured to be positionable on the flexible member and movable from a first orientation to a second orientation with respect to the flexible member, the fastener having a body with a first surface and a tapered portion defined by a leading end surface and the first surface, a second surface parallel to the first surface and defined by the leading end surface and a trailing end surface, and a longitudinal axis between the leading and trailing end surfaces, the first surface including a substantially flat portion configured to be positionable against a tissue section, and the fastener body including a bore extending between the first and second surfaces at an angle with respect to the longitudinal axis.

42. The tissue fixation system of claim 41 wherein the fastener includes a groove configured to reduce a profile of the fastener in the first orientation.

43. The tissue fixation system of claim 41 wherein the fastener is an anchor.

44. The tissue fixation system of claim 41 wherein the first and second surfaces are substantially parallel.

45. The tissue fixation system of claim 41 wherein the bore is substantially perpendicular to the first or second surface.

46. The tissue fixation system of claim 41 wherein the fastener includes at least a deformable portion.

47. The tissue fixation system of claim 41 wherein the leading or trailing end surface of the fastener is rounded.

48. The tissue fixation system of claim 41 wherein the leading or trailing end surface of the fastener is narrower than a majority of the fastener body.

* * * * *